(12) United States Patent
Han et al.

(10) Patent No.: US 8,518,462 B2
(45) Date of Patent: Aug. 27, 2013

(54) **COMPOUND COMPRISING EXTRACTS OR FRACTIONS OF *CHRYSANTHEMUM BOREALE* MAKINO HAVING ANTI-INFLAMMATION ACTIVITY**

(75) Inventors: Chang Soo Han, Seoul (KR); Won Tae Kim, Seoul (KR); Ho Young Choi, Seoul (KR); In Hye Ham, Seoul (KR); Gab Sik Yang, Seoul (KR); Chan Sung Bang, Hwaseong-si (KR)

(73) Assignees: Woongjin Coway Co., Ltd., Gongju-si (KR); University-Industry Cooperation Group of Kyung Hee University, Yongin-si (KR)

( * ) Notice: Subject to any disclaimer, the term of this patent is extended or adjusted under 35 U.S.C. 154(b) by 0 days.

(21) Appl. No.: 13/512,283

(22) PCT Filed: Sep. 30, 2010

(86) PCT No.: PCT/KR2010/006651
§ 371 (c)(1),
(2), (4) Date: May 25, 2010

(87) PCT Pub. No.: WO2011/065657
PCT Pub. Date: Jun. 3, 2011

(65) Prior Publication Data
US 2012/0276224 A1    Nov. 1, 2012

(30) Foreign Application Priority Data

| Nov. 27, 2009 | (KR) | 10-2009-0116247 |
| Apr. 13, 2010 | (KR) | 10-2010-0033965 |
| Jul. 16, 2010 | (KR) | 10-2010-0069145 |

(51) Int. Cl.
*A01N 65/00* (2009.01)

(52) U.S. Cl.
USPC .......................................................... 424/725

(58) Field of Classification Search
None
See application file for complete search history.

(56) References Cited

FOREIGN PATENT DOCUMENTS

| JP | 2001-122730 A | 5/2001 |
| KR | 10-2009-0003632 A | 1/2009 |

OTHER PUBLICATIONS

Kim et al., "Isolation of β-sitosterol, Phytol and Zingerone 4-O-β-D-glucopyranoside from *Chrysanthemum Boreale* Makino," *Korean J. Medicinal Crop Sci.* 13(5):284-287, 2005.

Cheng et al., "Anti-inflammatory and immunomodulatory activities of the extracts from the inflorescence of *Chrysanthemum indicum* Linné," *Journal of Ethno-Pharmacology* 101: 334-337.

Lim et al., "Isolation of Acetylcholinesterase Inhibitors from the Flowers of *Chrysanthemum indicum* Linne," *Food Sci Biotechnol* 16(2): 265-269, 2007.

*Primary Examiner* — Michael Meller
(74) *Attorney, Agent, or Firm* — Seed IP Law Group PLLC

(57) ABSTRACT

The present invention relates to a composition having an anti-inflammatory activity, comprising extracts or fractions of *Chrysanthemum boreale* Makino. Since the composition show the prophylactic and therapeutic effects on inflammatory diseases, in particular, atopic dermatitis, it can be used as a pharmaceutical composition, and also applied to various fields, including quasi-drugs, cosmetic compositions, foods, and water softeners.

5 Claims, 26 Drawing Sheets oral or topical administration(100,400mg/kg)
of Chrysanthemum boreale Makino extract(1%,2%)

⇧ shaving of the back skin

↑ application of 200ul of 0.5% DNCB dissolved in Aoo to
  the back skin of 6-week-old, male NC/Nga mice ▼ clinical scoring, ear thickness measurement ♡ blood and tissue collection Fig. 12
(a) p.o. (mg/kg)
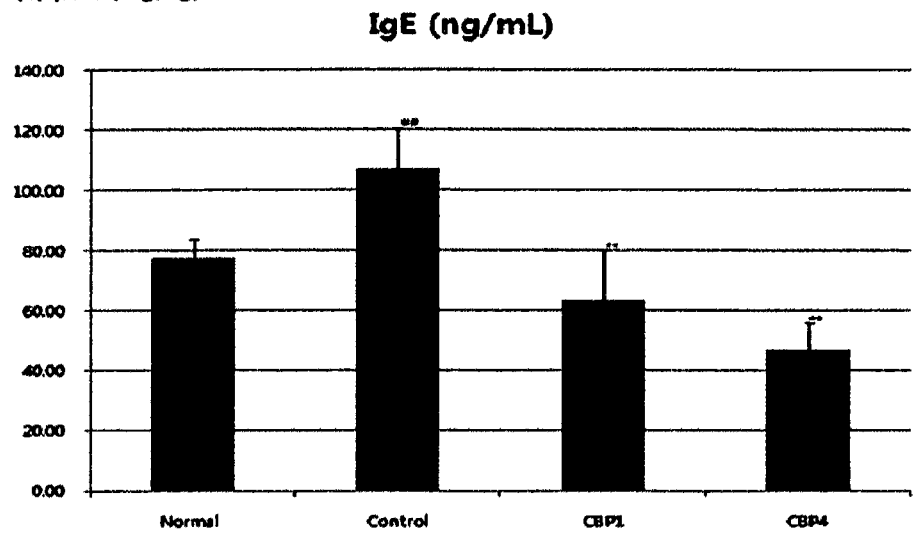
(b) smear (%)
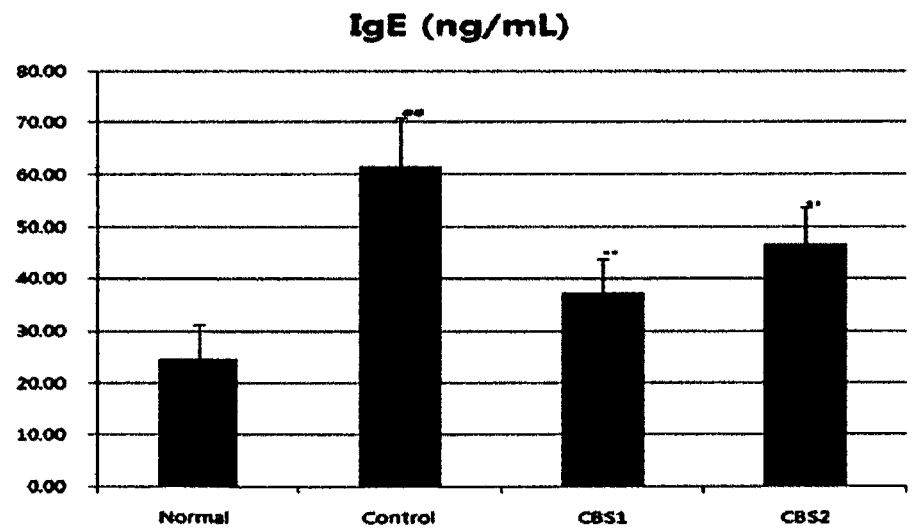

Fig. 15
Normal
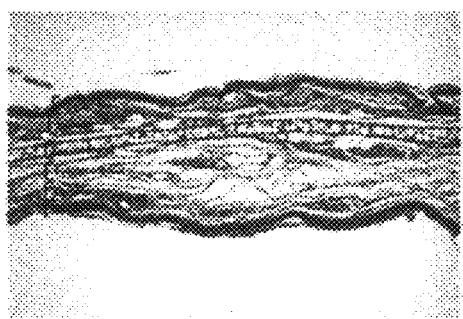
Control
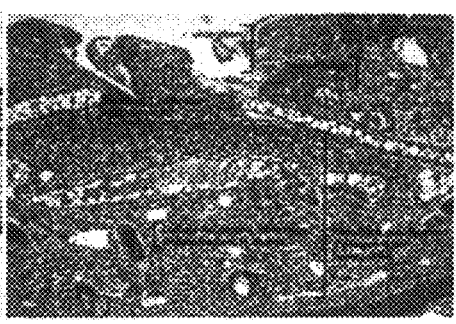
p.o. 100 mg/kg
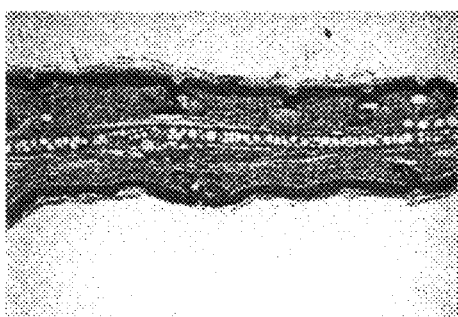
p.o. 400 mg/kg
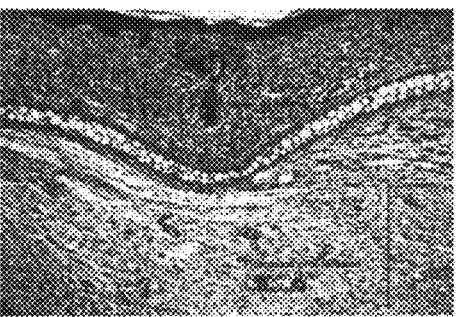
Smear 1%
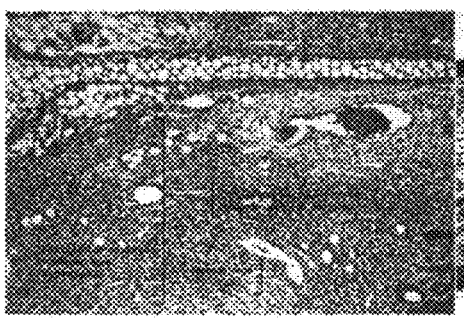
Smear 3%
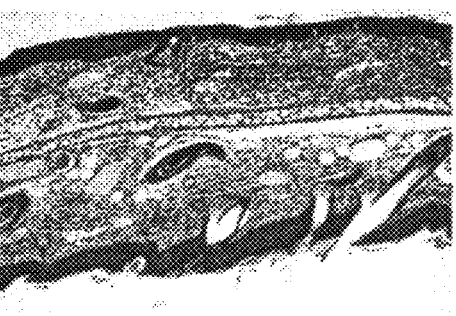

Fig. 24
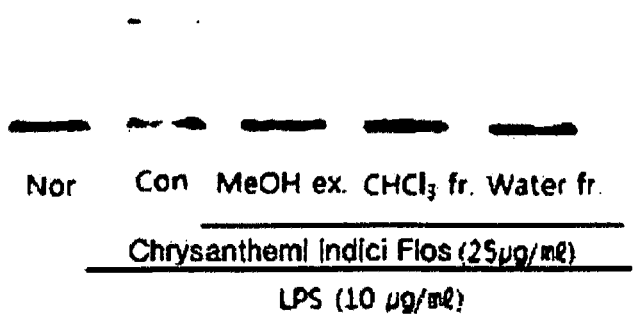
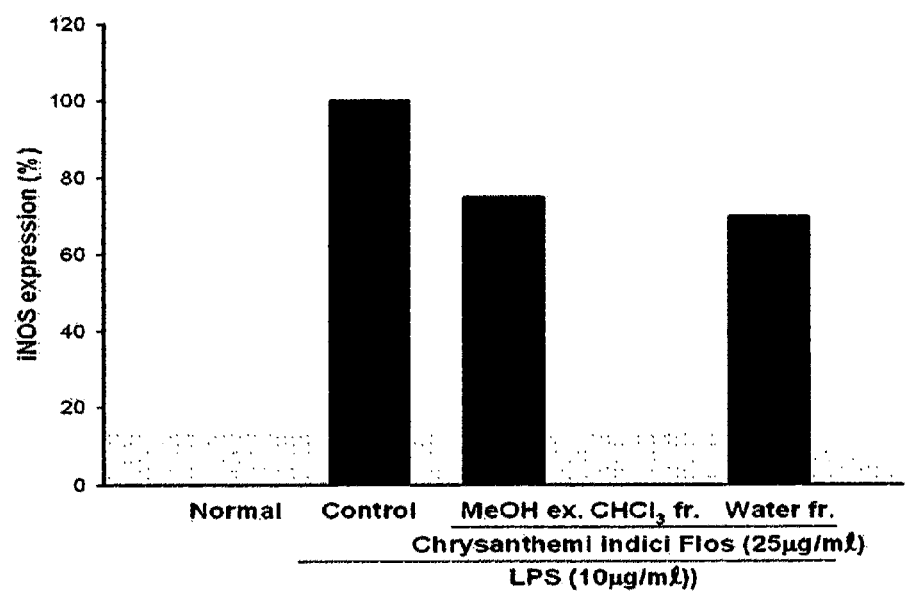
Fig. 25
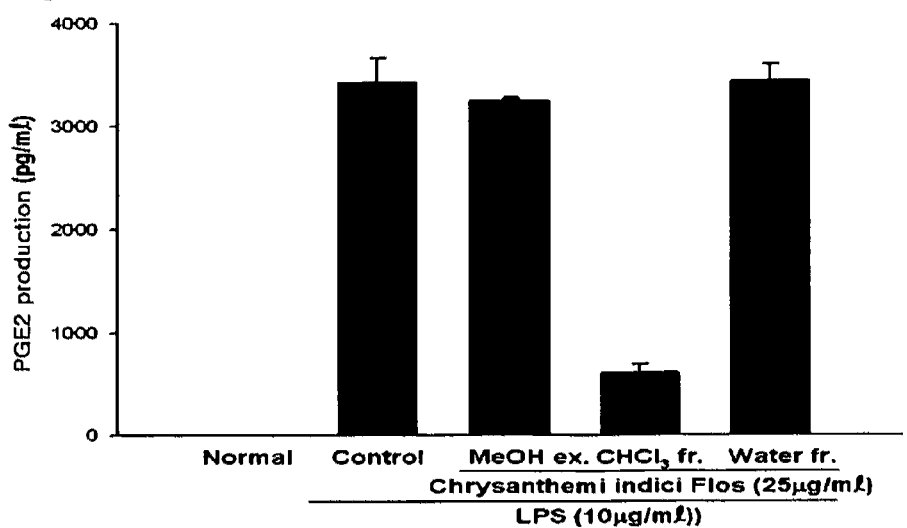

Fig. 26
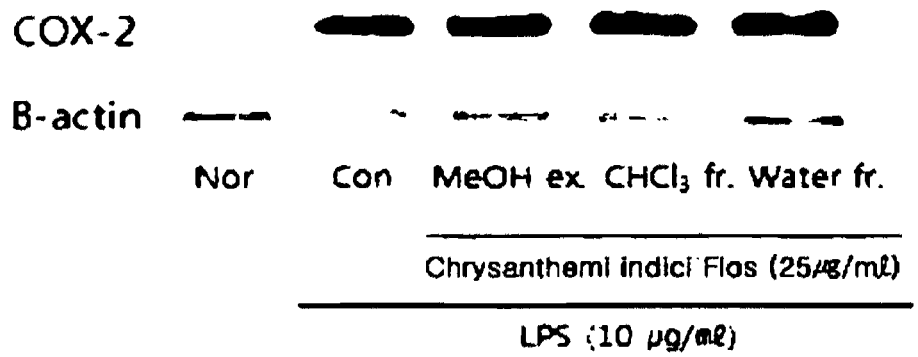
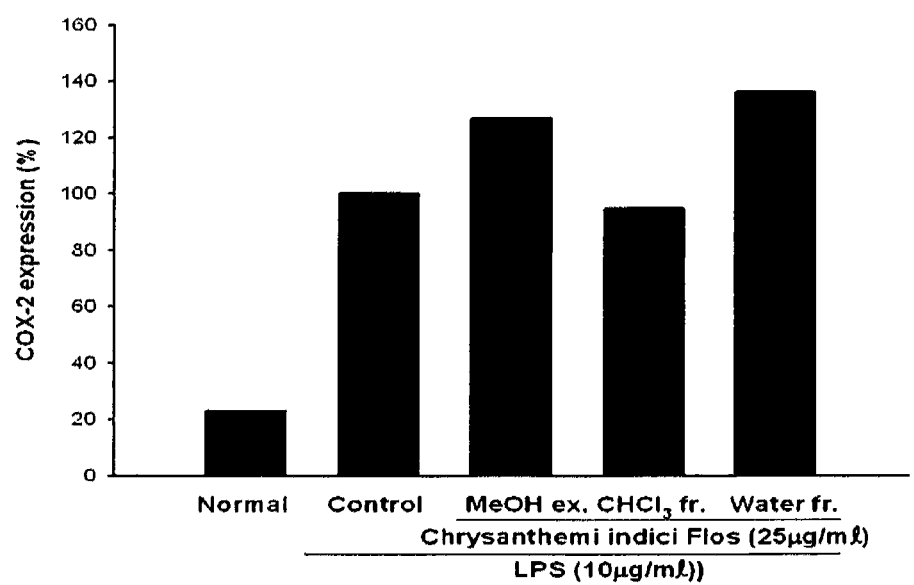

Fig. 27
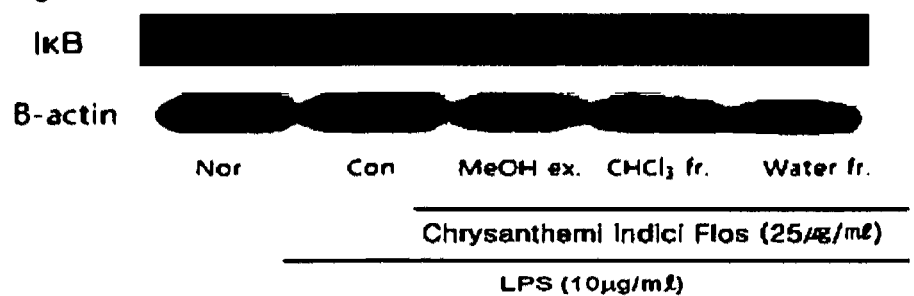
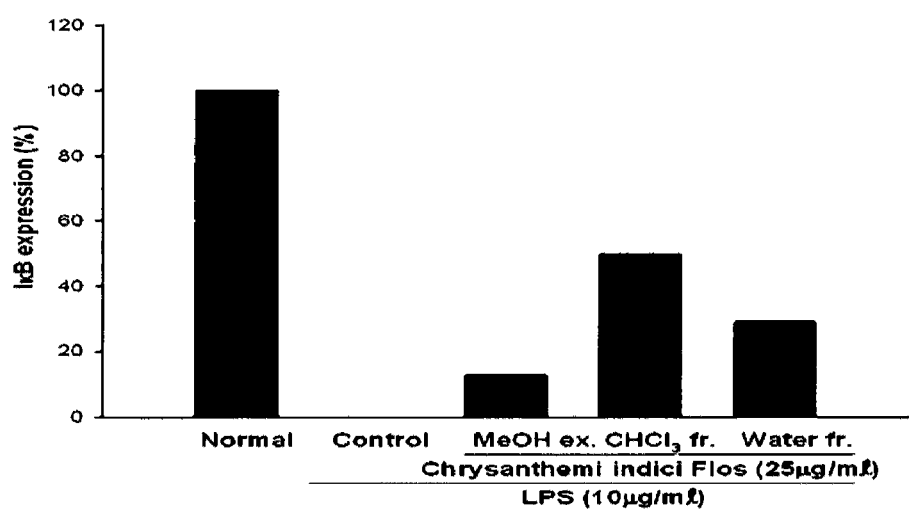

Fig. 28
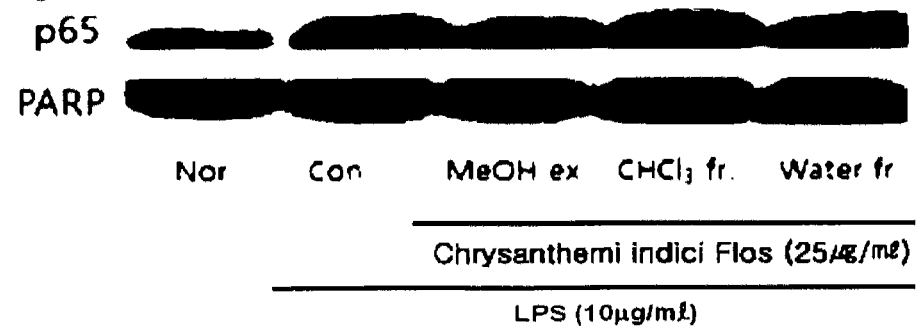
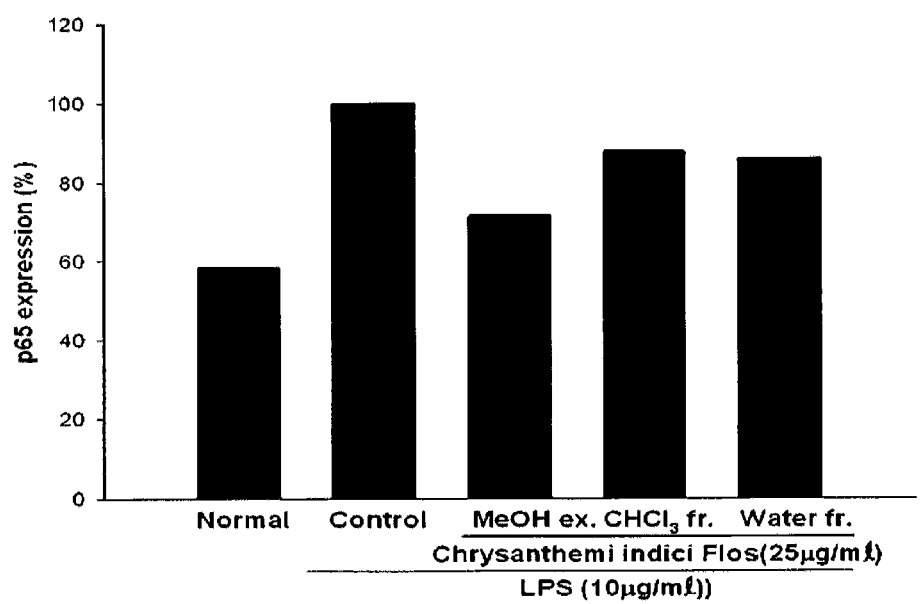

COMPOUND COMPRISING EXTRACTS OR FRACTIONS OF *CHRYSANTHEMUM BOREALE* MAKINO HAVING ANTI-INFLAMMATION ACTIVITY

TECHNICAL FIELD

The present invention relates to a composition having an anti-inflammatory activity, comprising extracts or fractions of *Chrysanthemum boreale* Makino.

BACKGROUND ART

Human skin undergoes changes with age due to various intrinsic and extrinsic factors. With respect to the intrinsic factors, the secretion of various hormones regulating metabolism is reduced, and the function of immune cells and the activity of cells are reduced, thus reducing the biosynthesis of immune proteins required in vivo and bioproteins. With respect to the extrinsic factors, environmental pollution and UV light cause various changes, including an increase in wrinkles, a reduction in elasticity, dry skin, and increases in melasma, freckles and age spots, leading to skin deterioration. These days, because most people want to look young and beautiful, they have a strong need to prevent or ameliorate skin aging due to extrinsic factors, such as UV and stress, as well as intrinsic factors.

One of the skin diseases, atopic dermatitis (AD) is a skin disorder with multifactorial etiology, such as immunological, genetic, pharmacological, physiological, and environmental factors, is caused in particular, by infections, stress, changes in season and climate, stimuli, and allergens. Atopic dermatitis is a chronic inflammation of the skin that occurs in persons of all ages, from infants to adults.

In general, approximately 80% of atopic dermatitis is associated with IgE, and atopic dermatitis can be categorized into the extrinsic (IgE-mediated) and the intrinsic (non-IgE-mediated) types. The elevated IgE response and eosinophilia are observed in patients with atopic dermatitis, which reflects increased responses of Th2 cytokines such as IL-4 and IL-5 with a concomitant decrease in the Th1 cytokine, IFN-γ production. In this connection, the use of various immunomodulators such as pime-crolimus and tacrolimus has been attempted. Especially, the presence of CD4+ CD25+ regulatory T cells (Treg cells) capable of directly suppressing immune responses has recently become known. Treg cells originate from the thymus and have an ability to control the activity of various T lymphocytes. Further, Treg cells transduce immune inhibitory signals or inhibit interaction between immune cells such as macrophages or B cells by the expression of CTLA4, GITR, CD25 and LAGS on their surface. Treg cells induce immune suppression through the production of cytokines such as TGF-β and IL-35, in addition to IL-10. In atopic dermatitis, Th2 cytokines such as IL-4 and IL-5 are highly produced due to defects in Th2 cell development, whereas the production of Th1 cytokines such as IFN-γ is suppressed. Recently, it was known that Th2 chemokines, represented by TARC/CCL17, MDC/CCL22, and CTACK/CCL2, directly affect Th2 cell development.

Cytokines are produced by various cells, and have many different actions. In particular, since an identical cytokine may exert different functions, cytokines are very difficult to classify. When T cells recognize antigens presented by macrophages and are activated to induce immune responses, numerous cytokines are involved in this process. Various cytokines are involved in each step of innate and adaptive immunity, from antigen recognition to effector steps, and some cytokines are also involved in the production of lymphocytes and other hemocytes. The actions of key cytokines are as follows.

IL-1 (interleukin 1) is a cytokine that is produced by activated mononuclear phagocytes, epithelial cells, or endothelial cells, and mediates inflammation. There are two forms of IL-1, IL-1α and IL-1β. A small amount of IL-1 activates CD4-T cells and B cells and stimulates inflammatory cells. However, an excessive amount of IL-1 functions as a hormone to induce fever and acute phase response.

IL-4 (interleukin 4) is a protein having a size of approximately 20 kDa, which is produced by CD4 T cells and activated mast cells, and functions as a B-cell growth factor. IL-4 also functions as a differentiation factor involved in immunoglobulin class switching in B cells, and may also activate CD4 T cells, mast cells, macrophages, etc.

IL-10 (interleukin 10) induces differentiation of activated T cells into CTLs by a synergistic effect with IL-2, and also induces proliferation of NK cells, LAK cells, and activated T cells.

IFN-γ (interferon-γ, also known as type II interferon, is produced by CD4 T cells or CD8 T cells to regulate immune responses, and is thus also called immune interferon. IFN-γ acts on T cells, B cells, NK cells, and endothelial cells to activate them, and functions as a macrophage-activating factor to increase the expression of MHC Class I and II. IFN-γ is also able to inhibit viral replication, like other interferons.

NO functions as a vasodilator under physiological conditions. However, when macrophages are stimulated by inflammatory cytokines, NO produced by iNOS induces inflammation under pathological conditions to increase COX-2 (cyclooxygenase-2) activity, leading to amplification of inflammation via arachidonic acid cascade.

COX-2 is a key modulator that produces prostaglandins from arachidonic acid. COX-2 converts arachidonic acid to PGG2. Depending on the enzymes, PGG2 is converted to PGE2, PGD2, PGF2, PGI2, or TXA2, which exert different functions in vivo. A representative COX-2 inhibitor is aspirin.

A recent research trend has focused on up- and down-regulation of IgE production by immune modulation, and the effects of clinically available, oriental herbal medicines on patients with atopic dermatitis have been actively studied. However, there is no report on the efficacy of *Chrysanthemum boreale* Makino on atopic dermatitis.

DISCLOSURE OF INVENTION

Technical Problem

Accordingly, the present inventors have demonstrated that the extracts and fractions of *Chrysanthemum boreale* Makino exhibit an effect of reducing serum IgE level and have an inhibitory effect on inflammation-related factors found in inflammatory diseases. On the basis of this study, they found that the extracts and fractions of *Chrysanthemum boreale* Makino show prophylactic and therapeutic effects on various inflammatory diseases, in particular, on atopic dermatitis, thereby completing the present invention.

Solution to Problem

It is an object of the present invention to provide a composition having an anti-inflammatory activity, comprising extracts or fractions of *Chrysanthemum boreale* Makino.

It is another object of the present invention to provide a pharmaceutical composition for the prevention or treatment of inflammatory diseases, and a cosmetic composition, a food composition, and a quasi-drug composition for the prevention or amelioration of inflammatory diseases, which include the composition comprising extracts or fractions of *Chrysanthemum boreale* Makino as an active ingredient.

It is still another object of the present invention to provide a water softener for the prevention or amelioration of inflammatory diseases, which includes a filter filler containing the composition comprising extracts or fractions of *Chrysanthemum boreale* Makino as an active ingredient.

It is still another object of the present invention to provide a method for preventing or treating inflammatory diseases by the administration of the composition comprising extracts or fractions of *Chrysanthemum boreale* Makino to patients with inflammatory diseases or at risk for inflammatory diseases.

Advantageous Effects of Invention

Since the composition according to the present invention has an anti-inflammatory activity, it can be used for the prevention or treatment of inflammatory diseases such as atopic dermatitis, and can also be applied to various fields, including quasi-drugs, cosmetics, foods, and water softeners.

BRIEF DESCRIPTION OF DRAWINGS

FIG. 12 (a) shows the results of measuring serum IgE level of atopic dermatitis-induced NC/Nga mouse model after oral administration of the extract of *Chrysanthemum boreale* Makino; (b) shows the results of measuring serum IgE level of atopic dermatitis-induced NC/Nga mouse model after topical administration of the extract of *Chrysanthemum boreale* Makino;

FIG. 15 shows photographs of ear tissue sections of atopic dermatitis-induced NC/Nga mouse model after treatment with the extract of *Chrysanthemum boreale* Makino;

FIG. 24 shows LPS-induced intracellular iNOS (induced nitric oxide synthase) production in RAW 264.7 cells after treatment with the fractions of *Chrysanthemi Indici Flos;*

FIG. 25 shows LPS-induced intracellular PGE2 production in RAW 264.7 cells after treatment with the fractions of *Chrysanthemi Indici Flos;*

FIG. 26 shows LPS-induced intracellular COX-2 production in RAW 264.7 cells after treatment with the fractions of *Chrysanthemi Indici Flos;*

FIG. 27 shows LPS-induced intracellular IκB production in RAW 264.7 cells after treatment with the fractions of *Chrysanthemi Indici Flos;*

FIG. 28 shows LPS-induced intracellular P65 production in RAW 264.7 cells after treatment with the fractions of *Chrysanthemi Indici Flos.

BEST MODE FOR CARRYING OUT THE INVENTION

Figure 1:
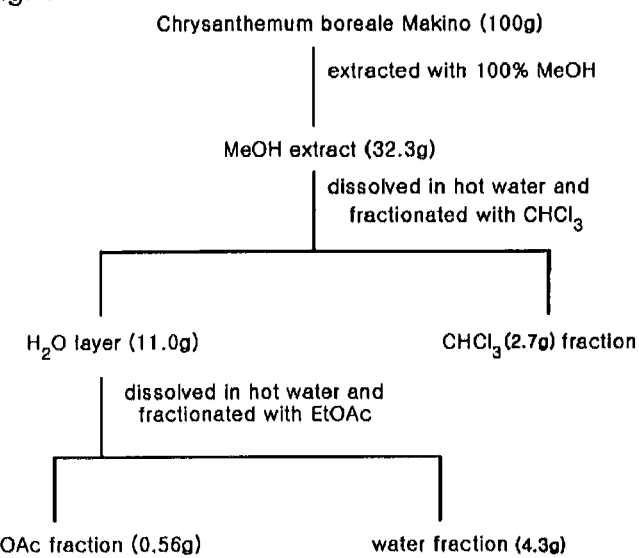
FIG. 1 is a flow chart showing the process of preparing the extracts and fractions of *Chrysanthemum boreale* Makino.

To achieve the above objects, in one aspect, the present invention provides a composition having an anti-inflammatory activity, comprising extracts or fractions of *Chrysanthemum boreale* Makino.

The present inventors have selected the extracts of *Chrysanthemum boreale* Makino, *Taraxacum mongolicum* Hand-mazz, *Phellodendron amurense* Rupr, *Acorus gramineus* Soland, *Ilex cornuta* Lindl, and *Prunus yedoensis* Matsumura, and examined their effects on inflammatory diseases. As a result, it was found that *Chrysanthemum boreale* Makino shows the most excellent effect. In accordance with the specific Experimental Example (Example 1), when atopic dermatitis-induced models were treated with the extracts of *Chrysanthemum boreale* Makino, *Taraxacum mongolicum* Hand-mazz, *Phellodendron amurense* Rupr, *Acorus gramineus* Soland, *Ilex cornuta* Lindl, and *Prunus yedoensis* Matsumura, and then clinical scoring was performed, it was found that the extracts of *Chrysanthemum boreale* Makino were recorded showing low scores for erythema, edema, excoriation, pruritus, dry skin, erosion, and lichenification (Tables 1 and 2, and FIGS. 4 and 5), and showed a remarkably low serum immunoglobulin E level, compared to the other plants (Table 3 and FIG. 6).

*Chrysanthemum boreale* Makino is a perennial plant, which belongs to the family Compositae and the order Campanulales, and is distributed in Korea, Japan, north China and Siberia, and is mainly found in valleys or fields. It grows to 1-1.5 m. Leaves are alternate, the bottom part falls when it blooms. The middle one is oblong, ovate, 5-7 cm long, 4-6 cm broad. The bottom part is cordate a bit or flat ended, and divided laminas have similar size, and are oblong, entire, sharp lobed serrates at the edge. Petiole is 1-2 cm long. The edge laminas are 2 pairs, and have a large gap between the laminas, hairs on the surface, and hairs in the middle of the backside. It is in flower from September to October, and the flower is 1.5 cm in diameter, and hangs on the end of the branches and main stems. The involucre is 4 mm long and 8 mm in diameter. The bract is in 3-4 lines, and the outer bract is linear or oblong and has hairs on its surface, and the inner bract is oblong and has a thin edge. Ligulate corolla is 5-7 mm long, yellow in color, and a tubular corolla's edge is divided into 5 parts. An achene is obovate and 1 mm long, and has 5-6 lines and no pappus, and ripens in October-November. Its stalk is 1-1.5 m tall and has many branches with short white hairs. Its roots come out and twigs stretch out. The plant grows well in any soil, in particular in fertile soil, and prefers dry to wet places.

The *Chrysanthemum boreale* Makino of the present invention is a scientific name, and may be purchased from commercially available sources, collected from nature, or cultivated. Further, the extracts of *Chrysanthemum boreale* Makino according to the present invention may be extracted from various organs of natural, hybrid, or mutant plants, for example, root, stalk, leaf, flower, fruit flesh and peel, and plant tissue culture, and is most preferably extracted from the flower of *Chrysanthemum boreale* Makino.

The extracts of *Chrysanthemum boreale* Makino according to the present invention may be obtained by extraction with water, an organic solvent or a solvent mixture thereof. Preferably, *Chrysanthemum boreale* Makino is dried for a predetermined time, and pulverized, followed by extraction according to the typical method known in the art, such as hot water extraction, cold water extraction, hot extraction, ultrasonic extraction, and cold extraction. The extraction method is not particularly limited, and it may be performed at room temperature or elevated temperature under the condition in which the active ingredients are not destroyed, or this destruction is minimized. Preferably, the powder of *Chrysanthemum boreale* Makino, obtained by pulverization of washed and dried *Chrysanthemum boreale* Makino, may be extracted using water, lower $C_1$-$C_4$ alcohol, or a solvent mixture thereof, and more preferably, it is extracted using water or methanol.

Hot water extraction of *Chrysanthemum boreale* Makino may be performed by the steps of heating *Chrysanthemum boreale* Makino with water, filtering *Chrysanthemum boreale* Makino, concentrating the filtrate and then pulverizing it with an excipient, and tabletting the extract powder of *Chrysanthemum boreale* Makino with a binder.

The excipient may be exemplified by starch, calcium carbonate, sucrose, lactose, or gelatin.

In addition, the binder may be exemplified by dextrin, hydroxypropyl methyl-cellulose, pregelatinized starch, povidone (polyvinylpyrrolidone), carboxymethyl cellulose, methylcellulose, or ethyl cellulose.

The extraction time is not particularly limited, but may be approximately 2 to 5 hrs, and hot water extraction may be performed at 70 to 100° C., preferably 80 to 100° C. Based on the weight of *Chrysanthemum boreale* Makino, 10 to 30-fold, preferably, 15 to 25-fold, and more preferably, approximately 20-fold volume of water may be used to prepare a hot water extract of *Chrysanthemum boreale* Makino.

Meanwhile, the fractions of *Chrysanthemum boreale* Makino of the present invention may be obtained by fractionation of the extract of *Chrysanthemum boreale* Makino. To obtain the fractions, a variety of solvents known in the art may be used, and preferably, organic solvents. For example, pentane, hexane, 2,2,4-trimethyl pentane, dicaine, cyclohexane, carbon disulfide, carbon tetrachloride, chlorobutane, diisopropyl ether, chloroform, acetone, nitropropane, butanone, dichloroethane, pyridine, propanol, methanol, and ethyl acetate are included. The preferred organic solvent includes non-polar organic solvents, in particular, chloroform, ethanol, ethyl acetate or a solvent mixture thereof, but is not limited thereto. In the specific Example of the present invention, chloroform, ethanol, or a solvent mixture thereof is used to obtain each fraction, and all fractions showed the activity. Among them, the chloroform fraction showed the highest anti-inflammatory activity (Tables 8, 9, and 10).

As used herein, the term "anti-inflammatory activity" means to inhibit inflammation, which is one of the body's internal defense mechanisms against certain stimulation, and refers to complicated lesions causing three changes: alteration of tissues, circulatory disturbances and exudation, and proliferation of tissues. More particularly, inflammation is part of innate immunity, and human innate immunity includes the perception of pathogens by recognition of specific cell-surface pattern, like in other animals. Phagocytes recognize the cells as non-self to attack pathogens. If pathogens penetrate physical barriers of the body, inflammation occurs. Inflammation is a non-specific defense that creates an environment hostile to microbes at the site of injury. In inflammatory responses, when injury occurs or pathogens invade the body, cytokines are released by the recruitment of leukocytes involved in initial immune responses. Thus, the intracellular cytokine level is an index of inflammatory activation.

The present inventors have performed experiments on *Chrysanthemum boreale* Makino, and demonstrated that the extracts and fractions of *Chrysanthemum boreale* Makino have an anti-inflammatory activity. In the specific Experimental Example (Example 3) of the present invention, the present inventors confirmed a reduction in serum IgE (immunoglobulin E), IFN-γ (interferon-γ), and IL-4 (interleukin-4) levels (FIGS. 12, 13, and 14); a reduction in intracellular NO (nitric oxide) level (FIG. 16); a reduction in iNOS (induced nitric oxide synthase) level (FIG. 17); a reduction in intracellular PGE2 (prostaglandin E2) level (FIG. 18); a reduction in intracellular COX-2 protein level (FIG. 19); and inhibition of IκB phosphorylation and a reduction in NF-κB nuclear translocation (FIGS. 20, 21, and 22) in inflammatory disease animal models after treatment with the extracts or fractions of *Chrysanthemum boreale* Makino. Since all of them are highly expressed during inflammatory or allergic responses, the reduction in their expression levels indicates that the extract of *Chrysanthemum boreale* Makino has an anti-inflammatory activity.

In particular, compared to *Chrysanthemi Indici Flos* which is a perennial plant belonging to the family Compositae, 60-90 cm long, with the dark red stalks, and has cracked pinnate leaves and fragrant yellow flowers blooming on the ends of the branches in October-November, each of the methanol (MeOH) extract, chloroform (CHCl3) fraction, and ethyl acetate (EtOAc) fraction of *Chrysanthemum boreale* Makino (5 μg/ml) was found to reduce the intracellular nitric oxide (NO) levels to approximately 38%, 78%, and 30% in inflammatory disease animal model (Example 3-2), whereas the methanol extract of *Chrysanthemi Indici Flos* was found to reduce the levels to 97.9%, 89.0%, 37.3%, and 17.8%, and the chloroform fraction of *Chrysanthemi Indici Flos* was found to reduce the levels to 50.6%, 19.2%, 16.6%, and 7.5% at the concentrations of 2.5 μg/ml, 25 μg/ml, 50 μg/ml, and 100 μg/ml, respectively (Table 14). This result indicates that a smaller amount of the extract of *Chrysanthemum boreale* Makino showed effects equivalent to or higher than that of *Chrysanthemi Indici. Flos*. In addition, when a reduction in iNOS (induced nitric oxide synthase) level (FIG. 24); a reduction in intracellular PGE2 (prostaglandin E2) level (FIG. 25); a reduction in intracellular COX-2 protein level (FIG. 26); and inhibition of IκB phosphorylation and a reduction in NF-κB nuclear translocation (FIGS. 27 and 28) were compared, the extracts and fractions of *Chrysanthemum boreale* Makino showed more excellent effect than those of *Chrysanthemi Indici Flos*, despite a lower content of *Chrysanthemum boreale* Makino.

Nitric oxide (NO) functions as a vasodilator under physiological conditions. However, when macrophages are stimulated by inflammatory cytokines, NO produced by iNOS induces inflammation under pathological conditions to increase COX-2 (cyclooxygenase-2) activity, leading to amplification of inflammation via arachidonic acid cascade.

IFN-γ, also known as type II interferon, is produced by CD4 T cells or CD8 T cells to regulate immune responses, and thus is also called immune interferon. IFN-γ acts on T cells, B cells, NK cells, and endothelial cells to activate them, and functions as a macrophage-activating factor to increase the expression of MHC Class I and II. IFN-γ is also able to inhibit viral replication, like other interferons.

IL-4 is a protein having a size of approximately 20 kDa, which is produced by CD4 T cells and activated mast cells, and functions as a B-cell growth factor. IL-4 also functions as a differentiation factor involved in immunoglobulin class switching in B cells, and may also activate CD4 T cells, mast cells, and macrophages.

In agreement with the above results, the extracts or fractions of *Chrysanthemum boreale* Makino according to the present invention have excellent prophylactic and therapeutic activities on inflammatory diseases, in particular, allergic inflammatory diseases.

The extracts and fractions of *Chrysanthemum boreale* Makino are not artificially-synthesized compounds, but based on the ingredients obtained from natural extracts. Thus, they are safe, non-toxic, and without side effects, and can be given over a long period of time. Further, the composition can be used for animals with inflammatory diseases, including monkeys, dogs, cats, rabbits, guinea pigs, rats, mice, cattle, sheep, pigs, and goats, as well as human.

Therefore, the present invention can be adopted for the preparation of a pharmaceutical composition for the prevention or treatment of inflammatory diseases comprising the extracts or fractions of *Chrysanthemum boreale* Makino as an active ingredient, and inflammatory diseases can be prevented or treated by the administration of the composition.

In another aspect of the present invention, the present invention relates to a pharmaceutical composition for the prevention or treatment of inflammatory diseases comprising the extracts or fractions of *Chrysanthemum boreale* Makino as an active ingredient, and a method for preventing or treating inflammatory diseases by the administration of the composition comprising extracts or fractions of *Chrysanthemum boreale* Makino to patients with inflammatory diseases or at risk for inflammatory diseases.

The inflammatory diseases may be allergic inflammatory diseases, and the allergic inflammatory diseases may include chronic obstructive pulmonary disease (COPD), asthma, rheumatoid arthritis, atopic dermatitis, and inflammatory bowel disease. However, any disease induced by inflammatory or allergic responses may be included without limitation, and preferably atopic dermatitis.

As used herein, the term "prevention" means all of the actions in which the disease is restrained or retarded by the administration of the composition comprising the extracts or fractions of *Chrysanthemum boreale* Makino according to the present invention.

As used herein, the term "treatment" means all of the actions in which the disease has taken a turn for the better or been modified favorably by the administration of the composition comprising the extracts or fractions of *Chrysanthemum boreale* Makino according to the present invention.

In accordance with the specific Experimental Example (Example 2) of the present invention, the present inventors confirmed 1) reduction in erythema, edema, excoriation, pruritus, dry skin, erosion, and lichenification (FIGS. 7 and 8); 2) reduction in ear edema (FIGS. 10 and 11); 3) reduction in scratching behavior (FIG. 9); and 4) inhibition of fibroblast proliferation, collagen layer hyperplasia, and ulceration, reduction in mast cell infiltration, and reduction in inflammation by neutrophil and lymphocyte infiltration (FIG. 15) in inflammatory disease animal models after treatment with the extracts of *Chrysanthemum boreale* Makino, indicating therapeutic effects on inflammatory disease, in particular, atopic dermatitis.

The pharmaceutical composition for the prevention or treatment of inflammatory diseases comprising the extracts or fractions of *Chrysanthemum boreale* Makino according to the present invention can be administered to mammals including rats, mice, livestock, and humans via various routes. All modes of administration are contemplated, for example, administration can be made orally, rectally or by intravenous, intramuscular, subcutaneous, epidural or intracerebroventricular injection. Preferably, the composition can be applied to the skin, and most preferably, oral administration.

The pharmaceutical composition for the prevention or treatment of inflammatory diseases of the present invention is administered in a pharmaceutically effective amount. As used herein, the term "pharmaceutically effective amount" refers to an amount sufficient for the treatment of diseases, which is commensurate with a reasonable benefit/risk ratio applicable for medical treatment. An effective dosage of the present composition may be determined depending on the subject and severity of the diseases, age, gender, type of infected virus, drug activity, the patient's drug sensitivity, administration time, administration routes, excretion rates, duration of treatment, simultaneously used drugs, and other factors known in the medical field. The effective amount may vary, as recognized by those skilled in the art, depending on route of administration, excipient usage, and co-usage with other active agents.

The pharmaceutical composition for the prevention or treatment of inflammatory diseases of the present invention may be used in the form of a pharmaceutically acceptable salt thereof, and also used singly or in combination with other pharmaceutically active compounds.

The pharmaceutical composition for the prevention or treatment of inflammatory diseases of the present invention may be prepared into a pharmaceutical formulation using the methods known in the art in order to provide rapid, prolonged or delayed release of the active ingredients after administration into mammals. In the preparation of formulations, it is preferable that the active ingredients may be mixed or diluted with carriers, or encapsulated in the container-type carrier.

Accordingly, the pharmaceutical composition for the prevention or treatment of inflammatory diseases of the present invention may be formulated into formulations for oral administration, such as powder, granule, tablet, capsule, suspension, emulsion, syrup, aerosol, etc., or as formulation for external application, suppository and sterile injectable solution, according to common methods. Suitable carrier, excipient, and diluent that are typically used in the preparation of composition may be further included.

Examples of the carrier, excipient, and diluent that may be included in the pharmaceutical composition of the present invention include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate and mineral oil. During formulation, commonly used filler, extender, binder, wetting agent, disintegrant, surfactant, etc. are used as diluent or excipient.

Solid formulations for oral administration include tablet, pill, powder, granule, capsule, or the like. The solid formulation is prepared by mixing the extract with at least one excipient, e.g., starch, calcium carbonate, sucrose, lactose, gelatin, etc. Also, lubricants such as magnesium stearate and talc may be used, in addition to the excipient.

Liquid formulations for oral administration include suspension, liquid for internal use, emulsion, syrup, or the like. In addition to commonly used simple diluents such as water and liquid paraffin, various excipients, e.g., wetting agent, sweetener, aromatic, preservative, etc., may be included.

Formulations for parenteral administration include sterilized aqueous solution, non-aqueous solution, suspension, emulsion, freeze-dried preparation and suppository. The non-aqueous solution or suspension may include propylene glycol, polyethylene glycol, vegetable oil such as olive oil, injectable ester such as ethyl oleate, or the like. A base for a suppository may be witepsol, macrogol, Tween 61, cocoa butter, laurin butter, glycerogelatin, etc.

In still another aspect, the present invention provides a food composition for the amelioration of inflammatory diseases, comprising the extracts or fractions of *Chrysanthemum boreale* Makino as an active ingredient.

The food composition of the present invention may be prepared in the forms of pills, powders, granules, infusion, tablets, capsules or drinks, and may be added to various foods, for example, drinks, gum, tea, a vitamin complex, health promoting foods, etc.

Besides the extracts or fractions of *Chrysanthemum boreale* Makino as an essential ingredient, the food composition of the present invention may include other ingredients without particular limitations, and may include various herb medicine extracts, food additives, or natural carbohydrates in the same manner of conventional foods.

The food composition may further include one or more herb medicine extracts selected from the group consisting of *Chrysanthemum boreale* Makino, *Taraxacum mongolicum* Hand-mazz, *Phellodendron amurense* Rupr, *Acorus gramineus* Soland, *Ilex cornuta* Lindl, and *Prunus yedoensis* Matsumura.

In addition, a food supplement additive may be further included, and food additives include a fragrance agent, a flavouring agent, a coloring agent, a filler, a stabilizer or the like, which is conventionally known in the art.

Examples of the natural carbohydrate include conventional sugar, such as monosaccharide (e.g., glucose, fructose, etc.); disaccharide (e.g., maltose, sucrose, etc.); polysaccharide (e.g., dextrin, cyclodextrin, etc.); and sugar alcohol such as xylitol, sorbitol, erythritol, etc. Also, as a fragrance agent, a natural fragrance agent such as thaumatin, a stevia extract (e.g., rebaudioside A, glycyrrhizin, etc.) and a synthetic fragrance agent such as saccharine, aspartame, etc. may be appropriately used.

In addition, the food composition of the present invention may contain various nutrients, vitamins, minerals (electrolytes), a flavor agent (such as a synthetic flavor agent, a natural flavor agent, etc.), a coloring agent, an extender (cheese, chocolate, etc.), pectic acid and salt thereof, alginic acid and salt thereof, organic acid, a protective colloid thickener, a PH adjuster, a stabilizer, a preservative, glycerin, alcohol, a carbonating agent used for a carbonated drink, etc. Also, the food composition of the present invention may include flesh that may be used for preparing natural fruit juice, fruit juice drinks, and vegetable drinks. Each of the above such ingredients may be used independently or in any combination thereof.

Further, there is no limit in applicable food, which is exemplified by meats, sausages, bread, chocolate, candies, snacks, cookies, pizza, ramyun, gums, ice cream, soups, beverages, tea, functional water, drinks, alcoholic drinks, and vitamin complex.

In still another aspect, the present invention relates to a cosmetic composition, which includes the composition comprising the extracts or fractions of *Chrysanthemum boreale* Makino as an active ingredient.

The cosmetic composition according to the present invention may formulated into cosmetic water, gel, water-soluble powder, oil-soluble powder, water-soluble liquid, cream, essence or the like, if necessary, to which pH-controlling substances, perfumes, emulsifiers, and antiseptics are added using conventional methods.

In still another aspect, the present invention relates to a quasi-drug composition, which includes the composition comprising the extracts or fractions of *Chrysanthemum boreale* Makino as an active ingredient. That is, the composition of the present invention may be added to a quasi-drug composition for the purpose of preventing or ameliorating inflammatory diseases.

When the extracts or fractions of *Chrysanthemum boreale* Makino of the present invention are used as the quasi-drug additive, the extracts or fractions may be added as it is, or may be used in combination with other quasi-drugs or quasi-drug ingredients according to the typical method. Mixed amounts of active ingredients may be suitably determined depending upon the purpose of use (prophylactic, health or therapeutic treatment). Preferably, the quasi-drug composition may be used in the preparation of disinfectant cleaner, shower foam, mouth freshener, wet tissue, cleaning soap, hand wash, humidifier filler, mask, ointment, coating agent, or filter filler. A filter including the filter filler according to the present invention may be applied to various fields, and used in any filtering apparatus known in the art.

Therefore, in still another aspect, the present invention provides a water softener for the prevention or amelioration of inflammatory diseases, comprising the filter filler.

As used herein, the term "water softener" is an appliance that is designed to remove cations such as calcium and magnesium from hard water, and is also called a hard water softener. In addition to water softening functions, it may include air refreshing functions and water purifying functions. The water softener of the present invention includes a filter filler containing the composition which comprises the extracts or fractions of *Chrysanthemum boreale* Makino as an active ingredient, thereby being effective for the prevention and amelioration of inflammatory diseases, in particular, atopic dermatitis. In addition to the extracts or fractions of *Chrysanthemum boreale* Makino, the water softener of the present invention may contain various ingredients including oriental herbal medicines, depending on the purpose.

MODE FOR THE INVENTION

Hereinafter, the present invention will be described in more detail with reference to the Examples. However, the following Examples are for the illustrative purpose only, and the invention is not limited by these Examples.

Example 1

Sample Extraction and Screening (1) Extraction of Drug Candidates 100 g each of *Chrysanthemum boreale* Makino, *Taraxacum mongolicum* Hand-mazz, *Phellodendron amurense* Rupr, *Acorus gramineus* Soland, *Ilex cornuta* Lindl, and *Prunus yedoensis* Matsumura were extracted using 100% methanol (MeOH) as a solvent in a 110° C. extractor three times, concentrated under reduced pressure using a rotary evaporator, and then freeze-dried to obtain each 100% methanol extract.

(2) Introduction of NC/Nga Mouse Model

NC/Nga mouse is known as a spontaneous atopic dermatitis mouse model, caused by enhanced IgE production due to hyperphosphorylation of JAK3 kinase. Recently, it was reported that atopic dermatitis is also spontaneously induced in STAT6 knockout NC/Nga mouse, in which STAT6 is essential for IgE and Th2 cytokine production, suggesting that dermatitis is induced by other unexpected mechanisms (J. I. 1999, 162: 1056-63). Despite these advantages, spontaneous dermatitis is induced at a low rate and there is a great difference in the severity of induced dermatitis. Actually, the mouse model is not a reliable model for evaluation. In Japan, therefore, the problem is solved by artificial induction of dermatitis using hapten, picryl chloride. However, use of picryl chloride is prohibited in Korea and thus, herein, DNCB (1-chloro 2,4-dinitrobenzene, Sigma 23732-9), structurally similar to picryl chloride, was used to perform the experiments, so as to obtain similar results.

In this model, major symptoms of atopic dermatitis (pruritus, increased IgE production, skin inflammation) were all observed, and furthermore, the symptoms were completely treated with topical steroid or oral cyclosporin, which is a well-known therapeutic agent for atopic dermatitis. Accordingly, NC/Nga mouse model was introduced as an in vivo model for efficacy evaluation of therapeutic agents for atopic dermatitis.

(3) Screening Method by using NC/Nga Mouse

The spontaneous atopic dermatitis mouse model, NC/Nga mouse was used to induce atopic dermatitis, and then evaluation was performed in the following manner to screen the most useful medicine. The drug screening was performed using the following experimental groups: a normal group which was not treated with DNCB so as not to develop atopic dermatitis, a control group which was treated with DNCB to develop atopic dermatitis, oral administration groups which were treated with the extract of *Chrysanthemum boreale* Makino (100 mg/kg, 400 mg/kg), and topical administration groups which were treated with the extract of *Chrysanthemum boreale* Makino (200 µl: 1% dilution, 2% dilution).

A. Clinical Scoring

Clinical scoring was performed twice each after DNCB (Sigma 23732-9) treatment, and treatment with candidate therapeutic agents (each 100 mg/kg and 400 mg/kg of *Chrysanthemum boreale* Makino, *Ilex cornuta* Lindl, *Phellodendron amurense* Rupr, *Taraxacum mongolicum* Hand-mazz, *Acorus gramineus* Soland, and *Prunus yedoensis* Matsumura). The clinical scoring of atopic dermatitis was performed and assessed by two or more experienced investigators. In particular, photographs were taken and stored, after completion of the drug treatment. The results of visual evaluation were expressed as the sum of individual scores of the following five items. The evaluation items include erythema, pruritus and dry skin, edema and excoriation, erosion, and lichenification, which were individually scored as follows: absent (0), slight (1), moderate (2), and severe (3). Thus, the scores range from 0 to 15. The scores before and after drug treatment were compared to determine the reduction ratio, which was compared to that of vehicle-treated group for significance test.

B. Scratching Behavior Evaluation

Immediately after drug administration, an index of itching and scratching behavior was examined for 30 min. Scratching with the hind limb was counted as one scratching behavior, and rapid and frequent scratching behavior within 1 sec was also counted as one scratching behavior.

C. Serum IgE Level

Serum IgE levels were determined by ELISA, after treating DNCB(Sigma 23732-9)-induced skin inflammation with the candidate therapeutic drugs (each 100 mg/kg and 400 mg/kg of *Chrysanthemum boreale* Makino, *Ilex cornuta* Lindl, *Phellodendron amurense* Rupr, *Taraxacum mongolicum* Hand-mazz, *Acorus gramineus* Soland, *Prunus yedoensis* Matsumura). The serum IgE levels before and after drug treatment were compared to determine the reduction ratio, which was compared to that of a vehicle-treated group for a significance test.

Figure 5:
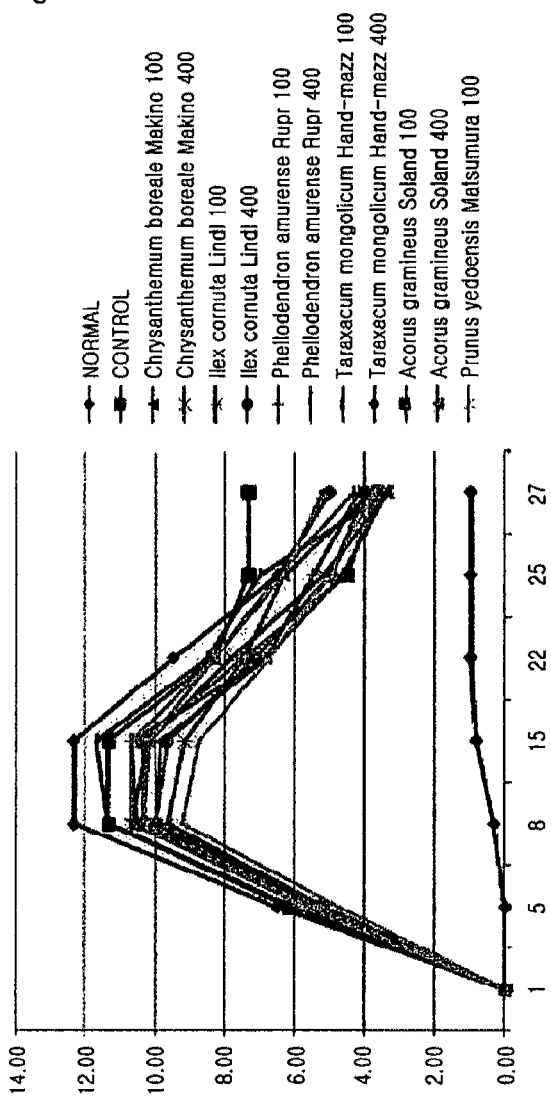
FIG. 5 shows the results of clinical scoring of atopic dermatitis-induced NC/Nga mouse model after treatment of the extracts of *Chrysanthemum boreale* Makino, *Taraxacum mongolicum* Hand-mazz, *Phellodendron amurense* Rupr, *Acorus gramineus* Soland, *Ilex cornuta* Lindl, and *Prunus yedoensis* Matsumura.

A. Drug-treated group: [IgE(drug) before treatment−IgE(drug) after treatment]/IgE(drug) before treatment B. Vehicle-treated group: [IgE(Vehicle) before treatment−IgE(Vehicle) after treatment]/IgE(vehicle) before treatment (4) Results A. Results of Clinical Scoring As a result of clinical scoring, lower scores were recorded for *Chrysanthemum boreale* Makino compared to other drugs candidates, and the scores were close to those of the normal group. Further, Table 1 shows the clinical scoring of atopic dermatitis-induced NC/Nga mouse model (FIG. 5).

TABLE 1

| (mg/kg) | 1 day | 5 day | 8 day | 15 day | 22 day | 25 day | 27 day |
|---|---|---|---|---|---|---|---|
| normal group | 0 ± 0 | 0 ± 0 | 0.3 ± 0.5 | 0.8 ± 1.3 | 1.0 ± 1.5 | 1.0 ± 1.5 | 1.0 ± 1.5 |
| control group | 0 ± 0 | 6.2 ± 0.8 | 11.3 ± 1.5 | 11.3 ± 0.8 | 8.3 ± 0.8 | 7.3 ± 0.8 | 7.3 ± 0.8 |
| Chrysanthemum boreale Makino 100-treated group | 0 ± 0 | 5.5 ± 2.1 | 10.0 ± 3.3 | 9.8 ± 2.4 | 6.8 ± 1.2 | 5.5 ± 2.3 | 4.2 ± 1.8 |
| Chrysanthemum boreale Makino 400-treated group | 0 ± 0 | 5.5 ± 1.1 | 10.7 ± 2.1 | 10.2 ± 1.7 | 7.8 ± 1.5 | 4.7 ± 1.0 | 3.4 ± 2.1 |
| Ilex cornuta Lindl 100-treated group | 0 ± 0 | 5.1 ± 1.5 | 9.6 ± 2.7 | 9.1 ± 2.2 | 7.5 ± 1.6 | 6.3 ± 0.5 | 3.8 ± 1.5 |
| Ilex cornuta Lindl 400-treated group | 0 ± 0 | 5.1 ± 1.2 | 10.0 ± 2.5 | 9.6 ± 1.8 | 7.1 ± 1.7 | 5.0 ± 2.1 | 4.0 ± 1.6 |
| Phellodendron amurense Rupr 100-treated group | 0 ± 0 | 5.5 ± 1.6 | 10.5 ± 3.1 | 10.6 ± 2.9 | 6.8 ± 1.8 | 5.5 ± 2.2 | 4.1 ± 1.8 |
| Phellodendron amurense Rupr 400-treated group | 0 ± 0 | 6.0 ± 1.6 | 11.3 ± 3.1 | 11.6 ± 2.9 | 8.5 ± 1.8 | 7.0 ± 2.2 | 3.3 ± 1.8 |
| Taraxacum mongolicum Hand-mazz 100-treated group | 0 ± 0 | 5.6 ± 1.0 | 10.6 ± 2.6 | 10.6 ± 1.9 | 8.3 ± 0.8 | 6.5 ± 0.8 | 4.3 ± 1.2 |
| Taraxacum mongolicum Hand-mazz 400-treated group | 0 ± 0 | 6.5 ± 0.5 | 12.3 ± 0.8 | 12.3 ± 0.8 | 9.5 ± 0.5 | 6.5 ± 0.5 | 5.0 ± 0.6 |
| Acorus gramineus Soland 100-treated group | 0 ± 0 | 5.1 ± 0.9 | 10.3 ± 1.9 | 10.3 ± 1.2 | 7.5 ± 1.5 | 4.5 ± 2.0 | 3.6 ± 1.6 |
| Acorus gramineus Soland 400-treated group | 0 ± 0 | 5.5 ± 1.3 | 10.3 ± 2.8 | 10.1 ± 2.4 | 8.3 ± 1.8 | 6.3 ± 1.0 | 5.1 ± 1.6 |
| Prunus yedoensis Matsumura 100-treated group | 0 ± 0 | 4.7 ± 0.5 | 9.2 ± 0.9 | 8.7 ± 1.2 | 6.7 ± 1.2 | 5.0 ± 1.6 | 3.7 ± 1.2 |

B. Results of Scratching Behavior

Figure 4:
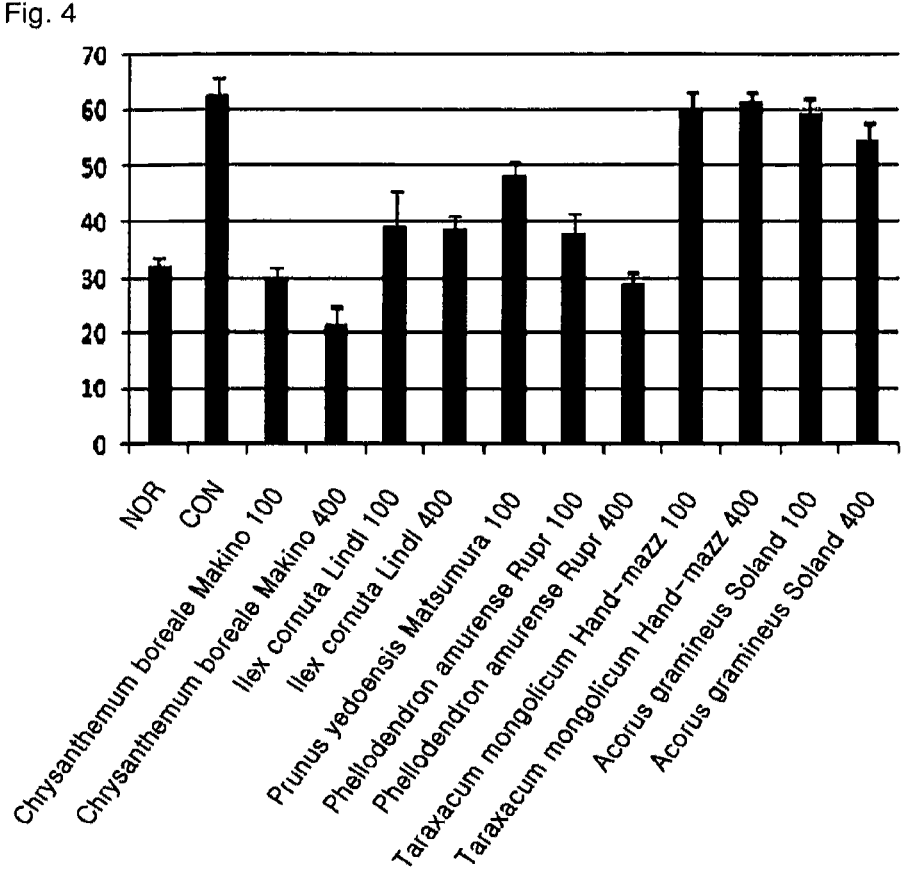
FIG. 4 shows changes in scratching behavior of atopic dermatitis-induced NC/Nga mouse model after treatment of the extracts of *Chrysanthemum boreale* Makino, *Taraxacum mongolicum* Hand-mazz, *Phellodendron amurense* Rupr, *Acorus gramineus* Soland, *Ilex cornuta* Lindl, and *Prunus yedoensis* Matsumura.

Table 2 shows changes in the scratching behavior of atopic dermatitis-induced NC/Nga mouse model. When an index of itching and scratching behavior was examined, 100 (mg/kg) and 400 (mg/kg) of *Chrysanthemum boreale* Makino were scored as 30.4±1.1 (point) and 21.8±2.8 (point), respectively. This result shows that the scores are remarkably lower than those of other drugs (FIG. 4).

TABLE 2

| (mg/kg) | scratching behavior (times) |
|---|---|
| normal group | 32.2 ± 1.4 |
| control group | 63.0 ± 2.9 |
| Chrysanthemum boreale Makino 100-treated group | 30.4 ± 1.1 |
| Chrysanthemum boreale Makino 400-treated group | 21.8 ± 2.8 |
| Ilex cornuta Lindl 100-treated group | 48.4 ± 2.1 |
| Ilex cornuta 4indl 100-treated group | 38.0 ± 3.4 |
| Phellodendron amurense Rupr 100-treated group | 60.4 ± 2.7 |
| Phellodendron amurense Rupr 400-treated group | 61.8 ± 1.5 |
| Taraxacum mongolicum Hand-mazz 100-treated group | 59.6 ± 3.1 |
| Taraxacum mongolicum Hand-mazz 400-treated group | 54.8 ± 3.1 |
| Acorus gramineus Soland 100-treated group | 52.6 ± 2.4 |
| Acorus gramineus Soland 400-treated group | 68.2 ± 2.4 |
| Prunus yedoensis Matsumura 100-treated group | 29.0 ± 1.9 |

C. Results of Serum IgE Levels

Figure 6:
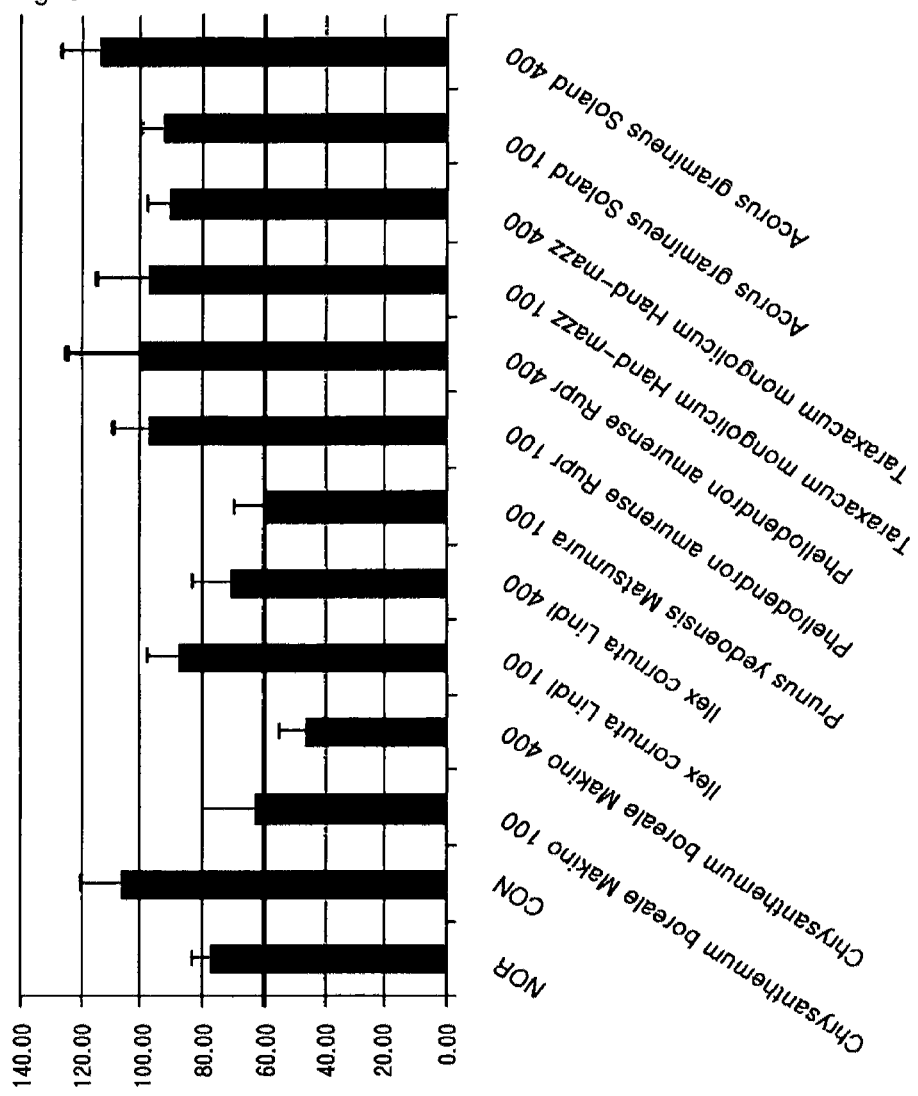
FIG. 6 shows changes in serum IgE level of atopic dermatitis-induced NC/Nga mouse model after treatment of the extracts of *Chrysanthemum boreale* Makino, *Taraxacum mongolicum* Hand-mazz, *Phellodendron amurense* Rupr, *Acorus gramineus* Soland, *Ilex cornuta* Lindl, and *Prunus yedoensis* Matsumura.

In serum IgE levels, lower scores were recorded for *Chrysanthemum boreale* Makino compared to other drugs candidates. 100 (mg/kg) and 400 (mg/kg) of *Chrysanthemum boreale* Makino were scored as 63.46±16.92 (ng/ml) and 46.99±8.88 (ng/ml), respectively. Table 3 shows changes in the serum IgE level of atopic dermatitis-induced NC/Nga mouse model (FIG. 6).

TABLE 3

| (mg/kg) | IgE(ng/ml) |
|---|---|
| normal group | 77.35 ± 6.62 |
| control group | 106.82 ± 13.36 |
| Chrysanthemum boreale Makino 100-treated group | 63.46 ± 16.92 |
| Chrysanthemum boreale Makino 400-treated group | 46.99 ± 8.88 |
| Ilex cornuta Lindl 100-treated group | 87.91 ± 10.97 |
| Ilex cornuta Lindl 400-treated group | 71.42 ± 12.83 |
| Phellodendron amurense Rupr 100-treated group | 98.08 ± 11.42 |
| Phellodendron amurense Rupr 400-treated group | 101.13 ± 23.74 |
| Taraxacum mongolicum Hand-mazz 100-treated group | 97.73 ± 18.07 |
| Taraxacum mongolicum Hand-mazz 400-treated group | 91.75 ± 6.65 |
| Acorus gramineus Soland 100-treated group | 92.88 ± 7.79 |
| Acorus gramineus Soland 400-treated group | 113.83 ± 12.91 |
| Prunus yedoensis Matsumura 100-treated group | 60.68 ± 9.44 |

Consequently, it can be seen that *Chrysanthemum boreale* Makino among the drug candidates showed the most significant effects in atopic dermatitis-induced NC/Nga mouse model, in accordance with the results of clinical scoring, scratching behavior, and serum IgE level. Therefore, *Chrysanthemum boreale* Makino was further studied on the basis of the above results. Detailed description and results of the experiments are as follows.

Example 2

Test on Atopic Dermatitis: NC/Nga Mouse Test 2-1. Experimental Method
(1) Introduction of NC/Nga Mouse Model
  NC/Nga mouse was used to test the effects of extracts and fractions of *Chrysanthemum boreale* Makino on major symptoms of atopic dermatitis (pruritus, increased IgE production, etc.).

(2) Extraction and Fractionation of *Chrysanthemum boreale* Makino 100 g of *Chrysanthemum boreale* Makino was extracted using 100% methanol (MeOH) as a solvent in a 110° C. extractor three times, concentrated under reduced pressure using a rotary evaporator, and then freeze-dried to obtain each 100% methanol extract. 32.3 g of the 100% methanol extracts of *Chrysanthemum boreale* Makino were dissolved in hot water, and then fractionated using chloroform and ethyl acetate. Then, each fraction was concentrated to obtain 4.3 g of water fraction, 2.7 g of chloroform fraction, and 0.56 g of ethyl acetate fraction (FIG. 1).

(3) Reagents and Instruments

1) Reagents

DNCB (Sigma 23732-9)
Olive oil (Shinyo Chemical 912193)
NC/Nga mouse (Central Lab. animal Inc., Korea)
Mouse IgE ELISA kit (SHIBAYAGI Co., Ltd, Japan)
IL-4 (R&D systems, Quantikine Immunoassay Kit, Minn. USA)
IFN-γ (R&D systems, Quantikine Immunoassay Kit, Minn. USA)
Regressive staining (Harris' hematoxylin, MUTO, Japan)
Eosin (MUTO, Japan)
Canada balsam (JUNSEI, Japan)

2) Instruments

ELISA Plate Reader: Versamax (Molecular Devices Co., USA)
Plate shaker: REO ROTOR (Hoefer Pharmacia Biotech Inc.)
Micrometer (IP65 coolant proof, #293-240, mitutoyo, Japan)
Microtome (HM325)
Clipper (JC-4005, JOAS Elec. CO., Korea)

(4) Induction of Atopic Dermatitis and Sample Treatment

1) Experimental Animal 5-week old NC/Nga mice used as experimental animals were supplied from Jung Ang Lab. Animal Inc., and after 1 week of acclimatization in the experimental facility, their body weight was measured (22±3 g). 6-8 mice were used for each group in the experiment. During the experimental period, animals were maintained at a temperature of 21±1° C. and humidity of 50±5% with free access to solid feed and water. One day before experiment, each animal's back, from the lower portion of the ear to top portion of the tail, was shaved using a clipper (JC-4005, JOAS Elec. CO., Korea) to remove hairs completely. All experimental animal procedures were conducted with the prior approval of the Kyung Hee University Animal Ethics Committee in accordance with the Guide for the Care and Use of Laboratory Animals.

Figure 2:
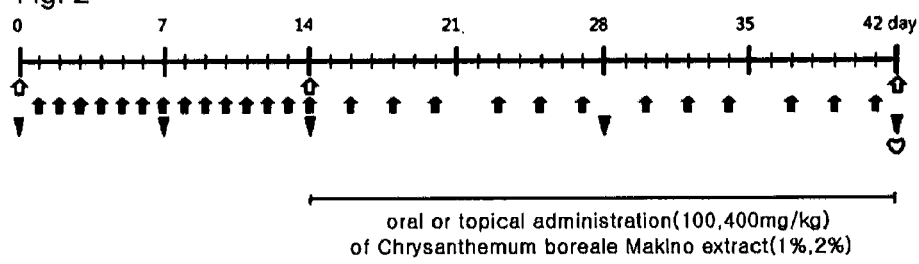
FIG. 2 shows a sensitization schedule of DNCB-treated NC/Nga mice.

2) Induction of Atopic Dermatitis and Sample Treatment 24 hrs after shaving the back of Nc/Nga mouse for the induction of atopic dermatitis, 200 μl of 0.5% DNCB (Sigma 23732-9) solution (acetone:olive oil=3:1) was applied to the shaved skin everyday for 2 weeks for immunization. 3 weeks after the initiation of sample administration, 200 μl of 0.5% DNCB solution was applied to the shaved skin three times a week to induce atopic dermatitis. The shaved back skin of each mouse was treated with DNCB for 2 weeks to induce atopic dermatitis, and then the sample was administered everyday for 4 weeks (oral and topical administration). 100 mg/kg and 400 mg/kg of the sample were orally administered, and 200 μl each of 1% and 2% dilutions was topically applied. Induction of atopic dermatitis and sample treatment procedures for DNCB-treated NC/Nga mice are illustrated in FIG. 2.

(5) Evaluation Method

A. Clinical Scoring

Atopic dermatitis of NC/Nga mouse was assessed by the clinical visual evaluation method generally used. Clinical scoring was performed immediately before DNCB treatment, during DNCB treatment, immediately before drug treatment, during drug treatment, and after termination of drug treatment, respectively. The clinical scoring of atopic dermatitis was performed and assessed by two or more experienced investigators. In particular, photographs were taken and stored, after completion of drug treatment. The results of visual evaluation were expressed as the sum of individual scores of the following five items. The evaluation items include erythema, pruritus and dry skin, edema and excoriation, erosion, and lichenification, which were individually scored as follows: absent (0), slight (1), moderate (2), and severe (3). Thus, the scores range from 0 to 15. The scoring of atopic dermatitis was performed and assessed by two or more experienced investigators. In particular, photographs were taken and stored, after completion of drug treatment.

B. Scratching Behavior Evaluation

Immediately after drug administration, an index of itching and scratching behavior was examined for 30 min. Scratching with the hind limb was counted as one scratching behavior, and rapid and frequent scratching behavior within 1 sec was also counted as one scratching behavior.

C. Ear Thickness Measurement

The ear thickness was measured at the middle of the right ear using a micrometer (IP65 coolant proof, #293-240, mitutoyo, Japan).

D. Determination of Serum IgE, IFN-γ and IL-4 levels

On the day the experiment was completed, blood was collected from the heart of the mouse, and then centrifuged at 5,000 rpm, 4° C. for 3 min to separate the serum. The serum was stored in −70° C. deep freezer until use, and thawed before use. Serum IgE, IL-4, and IFN-γ levels of Nc/Nga mice were determined using mouse ELISA kit (SHIBAYAGI Co., Ltd, Japan), IL-4 (R&D systems, Quantikine Immunoassay Kit, Minn. USA), and IFN-γ (R&D systems, Quantikine Immunoassay Kit, Minn. USA), respectively.

IgE level was determined in accordance with procedures of IgE mouse ELISA kit (SHIBAYAGI Co., Ltd, Japan). All reagents were prepared at room temperature, and immediately used.

A plate was washed with a washing buffer three times, and 50 μl of IgE standard solution or sample solution (sample 5 μl+buffer 45 μl) was aliquoted to each well, and gently mixed using a microplate shaker. The plate was incubated at room temperature (20-25° C.) for 2 hrs, and then washed with a buffer solution three times. 50 μl of biotin-conjugated anti-IgE antibody was aliquoted to each well, and gently mixed using a microplate shaker. The plate was incubated at room temperature for 2 hrs, and then washed with a washing buffer three times. 50 μl of HRP-avidin solution was aliquoted to each well, and gently mixed using a microplate shaker. The plate was incubated at room temperature for 1 hr. Subsequently, 50 μl of chromagenic substrate solution was aliquoted to each well, and gently mixed using a microplate shaker. The plate was incubated at room temperature for 20 min. Then, 50 μl of reaction stopper was added to each well and mixed well to stop further color development, and absorbance was measured at 450 nm within 30 min.

IL-4 and IFN-γ levels were determined in accordance with the procedures of IL-4 (R&D systems, Quantikine Immunoassay Kit, Minn. USA) and IFN-γ (R&D systems, Quantikine Immunoassay Kit, Minn. USA).

In accordance with the instructions, all reagents and samples were prepared, and all reagent solutions were maintained at room temperature, and the experiment was repeated twice. 50 µl of assay diluent RD1-18 (IL-4) or RD1-21 (IFN-γ was added to each well. 50 µl each of normal group, control group, and sample were added to each well, and the negative area was gently tapped to mix well for 1 min. The plate was covered, and incubated at room temperature for 2 hrs. The solution was completely removed from each well using an aspirator, and washed. This procedure was repeated five times. 100 µl of IL-4 (mouse IL-4 conjugate) or IFN-γ (IFN-γ Conjugate) was added to each well. The plate was covered with a new adhesive cover sheet, incubated at room temperature for 2 hrs, and then washed five times. 100 µl of substrate solution was added to each well, and incubated at room temperature for 30 min in the dark. 100 µl of stop solution was added to each well, and the plate was gently tapped to mix completely. Within 30 min, the absorbance of each well was measured at 450 nm with correction at 540 nm (or 570 nm).

E. Tissue Staining and Evaluation

After completion of the experiment, the mice were sacrificed and the back and ear tissues were removed and fixed in 10% neutral formalin. The tissues were embedded in paraffin to prepare paraffin-embedded blocks. The paraffin blocks were trimmed to a trimming thickness of 10 µm using a microtome (Microm-HM325), and then tissue sections were cut to a thickness of 3-4 µm. The obtained tissue sections were deparaffinized in xylene, immersed [100% alcohol (3 min) →90% alcohol (3 min)→80% alcohol (3 min)→70% alcohol (3 min)→D.W (3 min)], and stained [Harris' hematoxylin (4 min) washing 1% HCl alcohol (once)→washing (10 min) →eosin (10-20 sec)], and then dehydrated [70% alcohol (dipping)→80% alcohol (dipping)→95% alcohol (dipping) →100% alcohol (dipping)→100% alcohol (dipping)], and destained [xylene (3 min)→xylene (3 min)], followed by sealing.

In addition, to evaluate degree of inflammation, histological examination was performed to investigate the epidermal thickness of atopic dermatitis-induced skin, mast cell infiltration, eosinophil infiltration, neutrophil and lymphocyte infiltration, and fibroblast proliferation and collagen layer hyperplasia. The mast cells were stained with alcian blue and examined.

F. Statistical Analysis

A paired t-test was performed to compare the mean values before and after experiment. P<0.05, that is, less than 5% was considered statistically significant.

2-2. Experimental Results

A. Clinical Scoring Results

Figure 3:
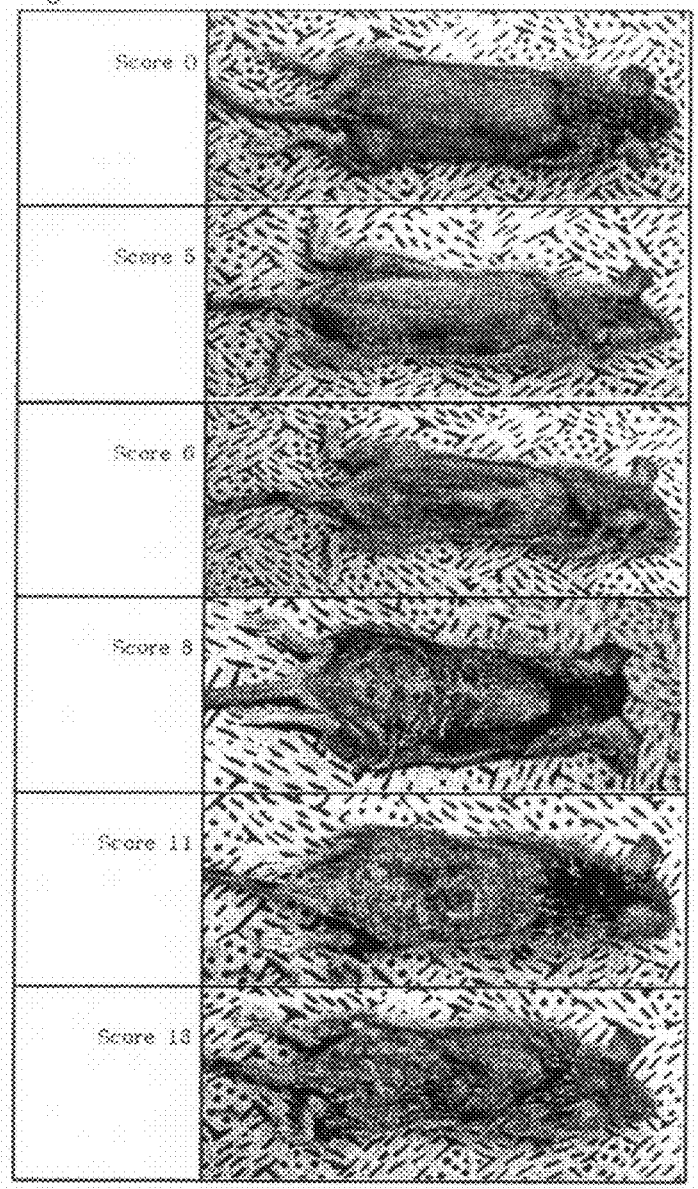
FIG. 3 shows changes of NC/Nga mouse model according to scores before and after drug treatment.

In total 6 groups of the normal group, DNCB-induced atopic dermatitis control group, oral administration groups (100 mg/mL and 400 mg/mL of extract of *Chrysanthemum boreale* Makino), and topical administration groups (200 µl of 1% and 2% extract of *Chrysanthemum boreale* Makino), atopic symptoms that occur in the back and ear of the mice were examined five times at one-week intervals. FIG. 3 was used as Reference index for clinical scoring.

Figure 7:
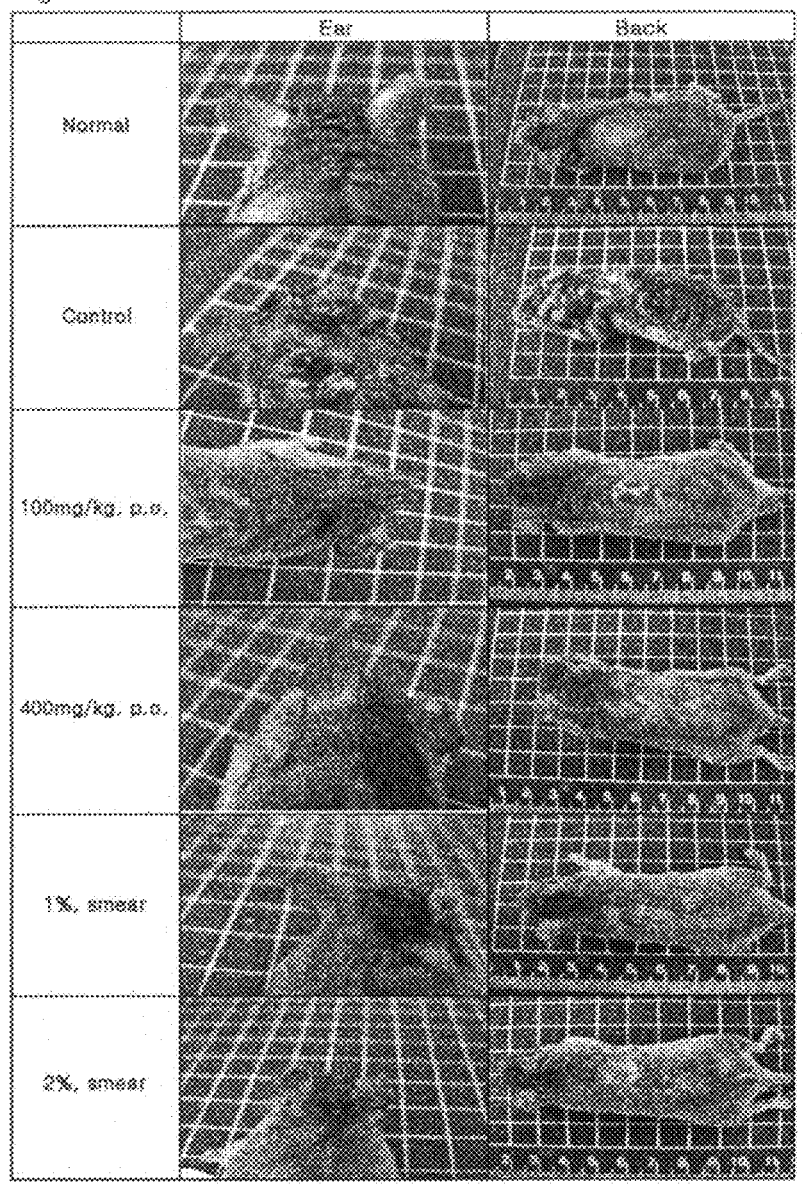
FIG. 7 shows changes in atopic symptoms of NC/Nga mouse model according to scores before and after treatment with the extract of *Chrysanthemum boreale* Makino.

The normal group had healthy skin, and the control group developed apparent atopic symptoms such as erythema, edema, scaling, incrustation, and lichenification. In the oral administration groups and topical administration groups, it was found that atopic symptoms were remarkably inhibited, compared to the control group, but a more rapid amelioration of atopic dermatitis was observed in the oral administration groups than the topical administration groups by visual examination (FIG. 7).

1 week after induction of atopic dermatitis, it was found that the clinical scores were recorded as 6.2±0.8 in the control group, 5.5±2.1 and 5.5±1.1 in the oral administration groups (100 mg/kg and 400 mg/kg of *Chrysanthemum boreale* Makino), and 5.2±1.0 and 5.5±1.4 in the topical administration groups (1% and 2% *Chrysanthemum boreale* Makino), respectively, indicating that atopic dermatitis was induced in all groups.

2 week after induction of atopic dermatitis, it was found that the clinical scores were recorded as 11.3±1.5 in the control group, 10.0±3.3 and 10.7±2.1 in the oral administration groups (100 mg/kg and 400 mg/kg of *Chrysanthemum boreale* Makino), and 10.3±2.0 and 10.3±2.8 in the topical administration groups (1% and 2% *Chrysanthemum boreale* Makino), respectively, indicating that the extract of *Chrysanthemum boreale* Makino did not yet show its effect.

4 weeks after induction of atopic dermatitis, that is, after 2-weeks of drug treatment, it was found that the clinical scores were recorded as 7.3±0.8 in the control group, 4.7±1.3 and 5.2±1.3 in the oral administration groups (100 mg/kg and 400 mg/kg of *Chrysanthemum boreale* Makino), indicating that the extract of *Chrysanthemum boreale* Makino began to show its effect and atopic dermatitis was significantly improved. However, the clinical scores were recorded as 7.5±1.5 and 8.3±1.9 in the topical administration groups (1% and 2% *Chrysanthemum boreale* Makino), indicating no improvement in atopic dermatitis.

6 weeks after induction of atopic dermatitis, that is, after 4-weeks of drug treatment, it was found that the clinical scores were recorded as 7.3±0.8 in the control group, 3.4±2.1 and 3.3±0.5 in the oral administration groups (100 mg/kg and 400 mg/kg of *Chrysanthemum boreale* Makino), and 4.5±2.1 and 6.3±1.0 in the topical administration groups (1% and 2% *Chrysanthemum boreale* Makino), respectively, indicating that atopic dermatitis was improved by the extract of *Chrysanthemum boreale* Makino.

Figure 8:
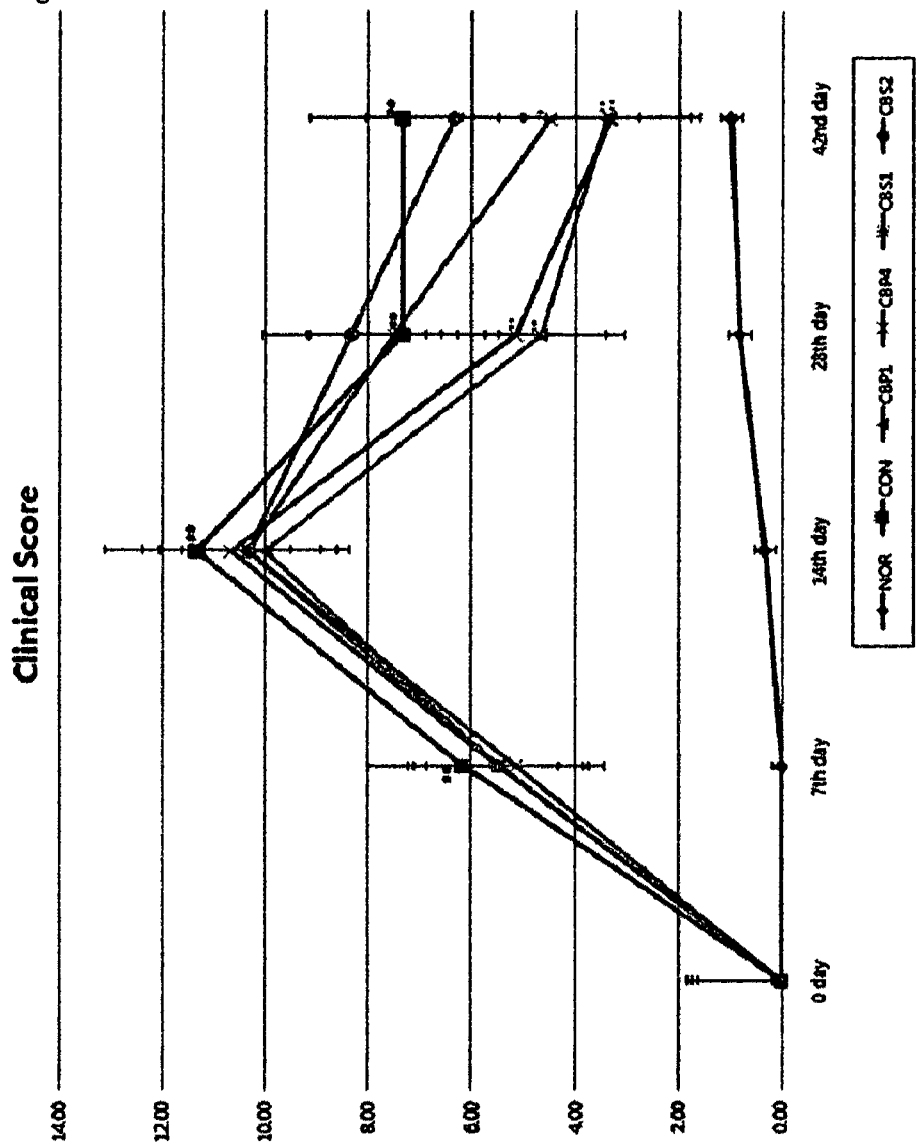
FIG. 8 shows the results of clinical scoring of atopic dermatitis-induced NC/Nga mouse model after treatment with the extract of *Chrysanthemum boreale* Makino.

In accordance with the experimental results, the normal group had healthy skin, and the atopic dermatitis-induced control group developed apparent atopic symptoms such as erythema, edema, scaling, incrustation, and lichenification. In the oral administration groups and topical administration groups, it was found that atopic symptoms were remarkably inhibited, compared to the atopic dermatitis-induced control group. However, 4 weeks after induction of atopic dermatitis, the improvement of atopic dermatitis was observed in the oral administration groups, and 6 week after induction of atopic dermatitis, the improvement of atopic dermatitis was observed in the topical administration groups, indicating a more rapid amelioration of atopic dermatitis in the oral administration groups than the topical administration groups (FIG. 8). That is, the oral administration groups showed a more effective improvement of atopic dermatitis than the topical administration groups.

In the following Table, NOR indicates the normal group, CON indicates the control group, CBP1 indicates the oral administration group (100 mg/kg of extract of *Chrysanthemum boreale* Makino), CBP4 indicates the oral administration group (400 mg/kg of extract of *Chrysanthemum boreale* Makino), CBS1 indicates the topical administration group (200 µl of 1% extract of *Chrysanthemum boreale* Makino), and CBS2 indicates the topical administration group (200 µl of 2% extract of *Chrysanthemum boreale* Makino). Table 4 shows the results of clinical scoring of atopic dermatitis-induced NC/Nga mouse model.

TABLE 4

| clinical score | | dose | 0 day | 7 day | 14 day | 28 day | 42 day |
|---|---|---|---|---|---|---|---|
| NOR | | | 0.0 ± 0.0 | 0.0 ± 0.0 | 0.3 ± 0.5 | 0.8 ± 1.3 | 1.0 ± 1.6 |
| CON | | | 0.0 ± 0.0 | 6.2 ± 0.8[##] | 11.3 ± 1.5[##] | 7.3 ± 0.8[##] | 7.3 ± 0.8[##] |
| CBP1 | oral administration | 100 mg/kg | 0.0 ± 0.0 | 5.5 ± 2.1 | 10.0 ± 3.3 | 4.7 ± 1.3** | 3.4 ± 2.1** |
| CBP4 | oral administration | 400 mg/kg | 0.0 ± 0.0 | 5.5 ± 1.1 | 10.7 ± 2.1 | 5.2 ± 1.3** | 3.3 ± 0.5** |
| CBS1 | topical administration | 1% | 0.0 ± 0.0 | 5.2 ± 1.0 | 10.3 ± 2.0 | 7.5 ± 1.5 | 4.5 ± 2.1** |
| CBS2 | topical administration | 2% | 0.0 ± 0.0 | 5.5 ± 1.4 | 10.3 ± 2.8 | 8.3 ± 1.9 | 6.3 ± 1.0* |

All the data are expressed as mean ± SD (N = 5).
[##]$p < 0.01$, comparison with normal group
*$p < 0.05$,
**$p < 0.01$, comparison with control group B. Results of Scratching Behavior Scratching behavior of mice was observed as 63.0±2.9 times per 30 min in the control group, 30.4±1.4 times per 30 min and 21.8±2.9 times per 30 min in the oral administration groups (100 mg/kg and 400 mg/kg of *Chrysanthemum boreale* Makino), and 45.4±2.7 times per 30 min and 45.0±3.4 times per 30 min in the topical administration groups (1% and 2% *Chrysanthemum boreale* Makino).

Figure 9:
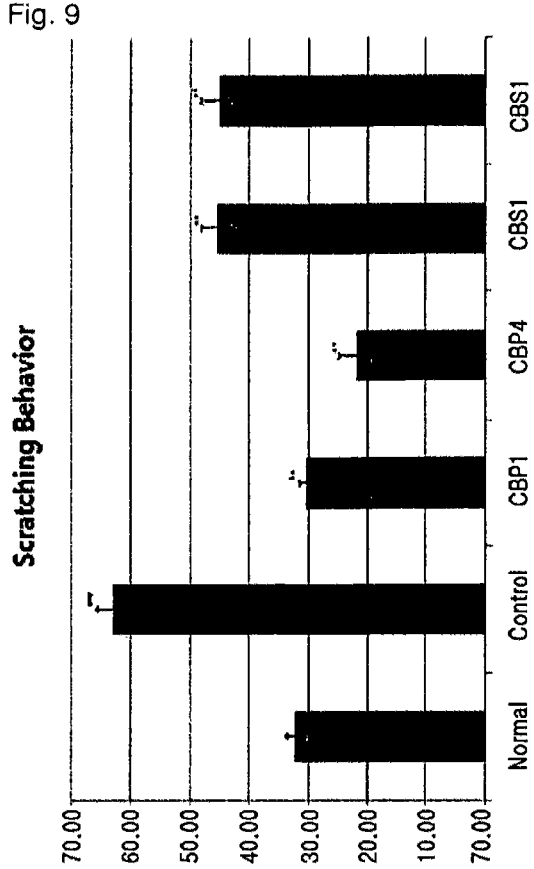
FIG. 9 shows the results of scratching behavior of atopic dermatitis-induced NC/Nga mouse model after treatment with the extract of *Chrysanthemum boreale* Makino.

A reduction in scratching behavior was observed in all treated groups, and scratching behavior was inhibited in the oral and topical administration groups at a ratio of approximately 51-65% and 28-29% (FIG. 9). Table 5 shows the results of scratching behavior of atopic dermatitis-induced NC/Nga mouse model.

TABLE 5

| | | dose | scratching behavior (times) |
|---|---|---|---|
| Normal | — | — | 32.2 ± 1.5 |
| Control | — | — | 63.0 ± 2.9[##] |
| CBP1 | oral administration | 100 mg/kg | 30.4 ± 1.4** |
| CBP4 | oral administration | 400 mg/kg | 21.8 ± 2.9** |
| CBS1 | topical administration | 1% | 45.4 ± 2.74** |
| CBS2 | topical administration | 2% | 45.0 ± 3.4** |

Figure 10:
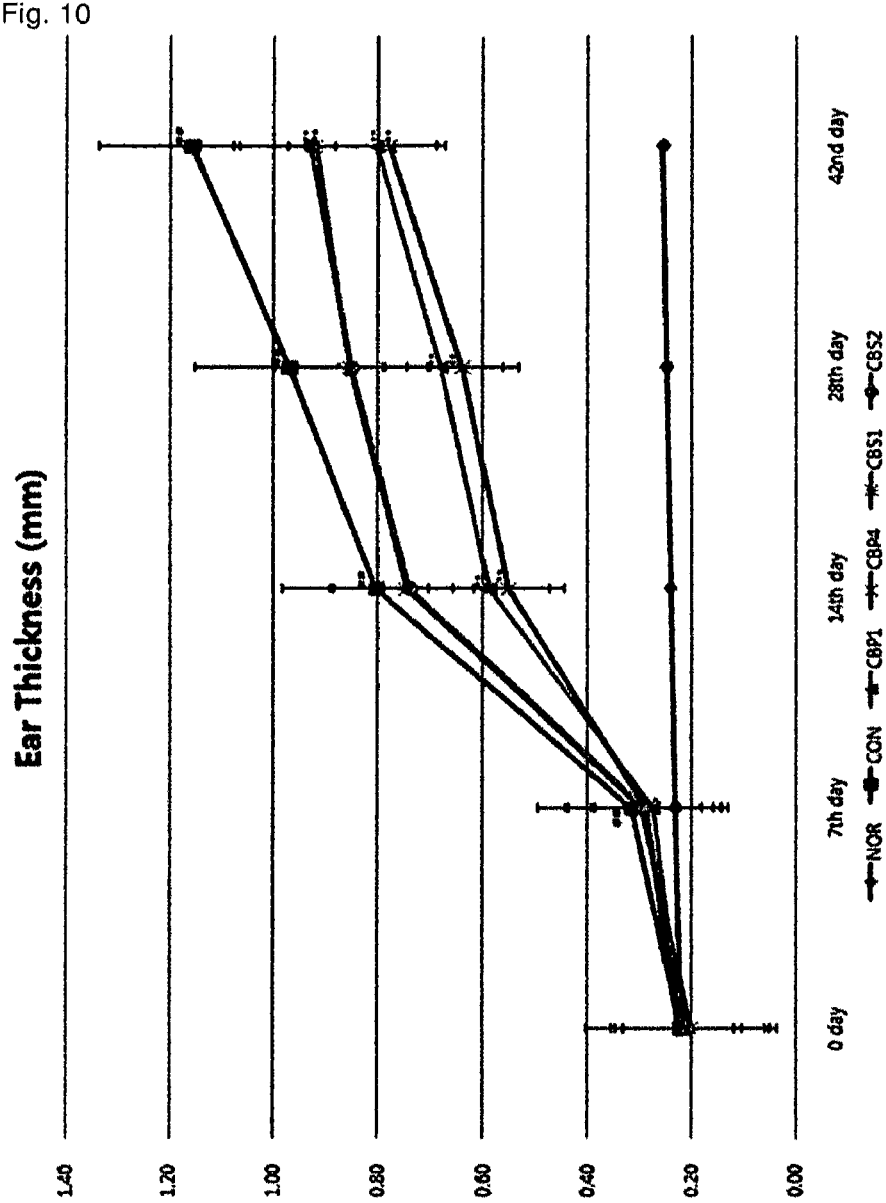
FIG. 10 shows the results of measuring ear thickness (length: mm) of atopic dermatitis-induced NC/Nga mouse model after treatment with the extract of *Chrysanthemum boreale* Makino.
Figure 11:
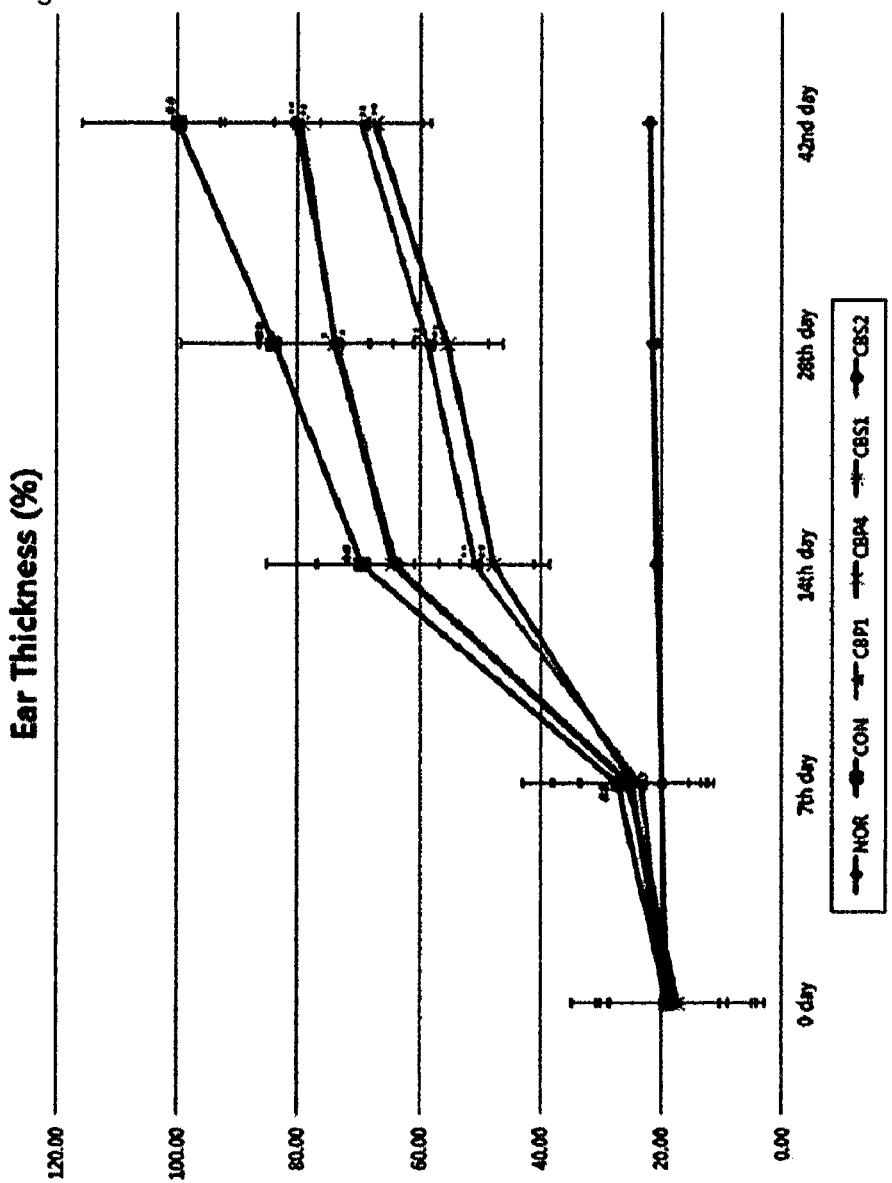
FIG. 11 shows the results of measuring ear thickness (volume: %) of atopic dermatitis-induced NC/Nga mouse model after treatment with the extract of *Chrysanthemum boreale* Makino.

All the data are expressed as mean ± SD (N = 5).
[##]$p < 0.01$, comparison with normal group
*$p < 0.05$,
**$p < 0.01$, comparison with control group C. Results of Epidermal Thickness of Atopic Dermatitis-Induced Tissue—Effect on Ear Edema To measure edema, the ear thickness of mice was measured every week after the initiation of experiment until the termination of experiment. There was no change in the ear thickness of the normal group, but a significant increase in the ear thickness was found in atopic dermatitis-induced control group. Inhibition of ear edema was observed in the oral and topical administration groups of *Chrysanthemum boreale* Makino. In particular, a remarkable inhibition of ear edema was observed in the oral administration groups. Table 6 (upper and lower Tables) shows the results of measuring ear thickness of atopic dermatitis-induced NC/Nga mouse model (FIGS. 10 and 11).

TABLE 6

| ear thickness | | dose | 0 day (mm) | 7 day (mm) | 14 day (mm) | 28 day (mm) | 42 day (mm) |
|---|---|---|---|---|---|---|---|
| NOR | | | 0.22 ± 0.02 | 0.23 ± 0.02 | 0.24 ± 0.02 | 0.25 ± 0.03 | 0.26 ± 0.01 |
| CON | | | 0.22 ± 0.02 | 0.31 ± 0.03[##] | 0.80 ± 0.01[##] | 0.97 ± 0.06[##] | 1.16 ± 0.06[##] |
| CBP1 | oral administration | 100 mg/kg | 0.22 ± 0.03 | 0.27 ± 0.02* | 0.59 ± 0.03** | 0.68 ± 0.04** | 0.80 ± 0.05** |
| CBP4 | oral administration | 400 mg/kg | 0.22 ± 0.03 | 0.29 ± 0.03 | 0.55 ± 0.02** | 0.64 ± 0.04** | 0.78 ± 0.06** |
| CBS1 | topical administration | 1% | 0.20 ± 0.02 | 0.29 ± 0.03 | 0.74 ± 0.08 | 0.85 ± 0.05** | 0.92 ± 0.04** |
| CBS2 | topical administration | 2% | 0.21 ± 0.02 | 0.29 ± 0.03 | 0.74 ± 0.07 | 0.85 ± 0.07* | 0.93 ± 0.04** |

| ear thickness | | dose | 0 day (%) | 7 day (%) | 14 day (%) | 28 day (%) | 42 day (%) |
|---|---|---|---|---|---|---|---|
| NOR | | | 19.0 ± 1.9 | 19.9 ± 1.9 | 20.8 ± 1.6 | 21.4 ± 2.3 | 22.1 ± 0.9 |
| CON | | | 19.0 ± 1.4 | 27.2 ± 2.2[##] | 69.4 ± 1.1[##] | 83.9 ± 5.3[##] | 100.0 ± 5.1[##] |
| CBP1 | oral administration | 100 mg/kg | 19.0 ± 2.2 | 23.5 ± 1.7* | 50.9 ± 3.3** | 58.7 ± 3.5** | 69.6 ± 4.0** |
| CBP4 | oral administration | 400 mg/kg | 19.4 ± 2.3 | 24.7 ± 2.5 | 47.8 ± 2.1** | 55.4 ± 3.6** | 67.3 ± 4.5** |
| CBS1 | topical administration | 1% | 17.3 ± 1.4 | 25.4 ± 2.6 | 64.4 ± 6.7 | 73.9 ± 4.4** | 79.6 ± 3.5** |
| CBS2 | topical administration | 2% | 18.0 ± 1.4 | 25.1 ± 2.9 | 63.8 ± 6.1 | 73.5 ± 6.0* | 80.4 ± 3.3** |

All the data are expressed as mean ± SD (N = 5).
[##]$p < 0.01$, comparison with normal group
*$p < 0.05$,
**$p < 0.01$, comparison with control group D. Results of Serum IgE, IFN-γ and IL-4 Levels Table 7 shows the results of ELISA to determine serum IgE, IFN-γ and IL-4 levels in atopic dermatitis-induced mouse by DNCB sensitization and attack.

① Determination of Serum IgE Level

In oral administration experiment, serum IgE levels were 106.8±13.4 ng/ml in the control group, and 63.5±16.9 ng/ml and 47.6±8.9 ng/ml in the oral administration groups (100 mg/kg and 400 mg/kg of *Chrysanthemum boreale* Makino), indicating a significant reduction (P=0.001)(FIG. 12 (*a*)). In topical administration experiment, serum IgE levels were 61.6±9.3 ng/ml in the control group, and 37.2±6.6 ng/ml and 46.7±7.1 ng/ml in the topical administration groups (1% and 2% *Chrysanthemum boreale* Makino), indicating a reduction in the level (FIG. 12 (*b*)).

② Determination of Serum IFN-γ Level

Figure 13:
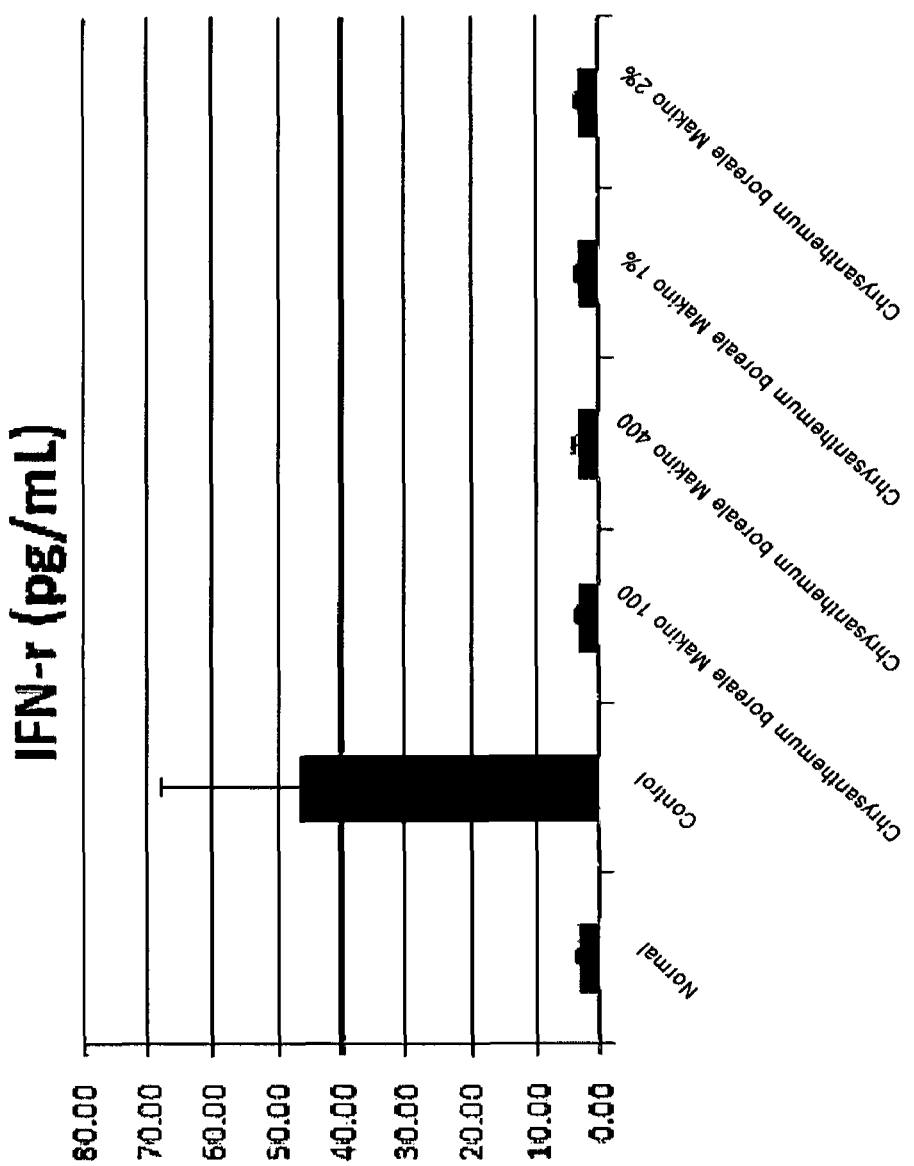
FIG. 13 shows the results of measuring serum IFN-γ level of atopic dermatitis-induced NC/Nga mouse model after treatment with the extract of *Chrysanthemum boreale* Makino.

Serum IFN-γ levels were 46.7±21.5 pg/ml in the control group, 3.3±0.4 pg/ml and 3.5±0.5 ng/ml in the oral administration groups (100 mg/kg and 400 mg/kg of *Chrysanthemum boreale* Makino), and 3.5±0.4 pg/ml and 3.6±0.4 pg/ml in the topical administration groups (1% and 2% *Chrysanthemum boreale* Makino), indicating a significant reduction (FIG. 13).

③ Determination of Serum IL-4 Level

Figure 14:
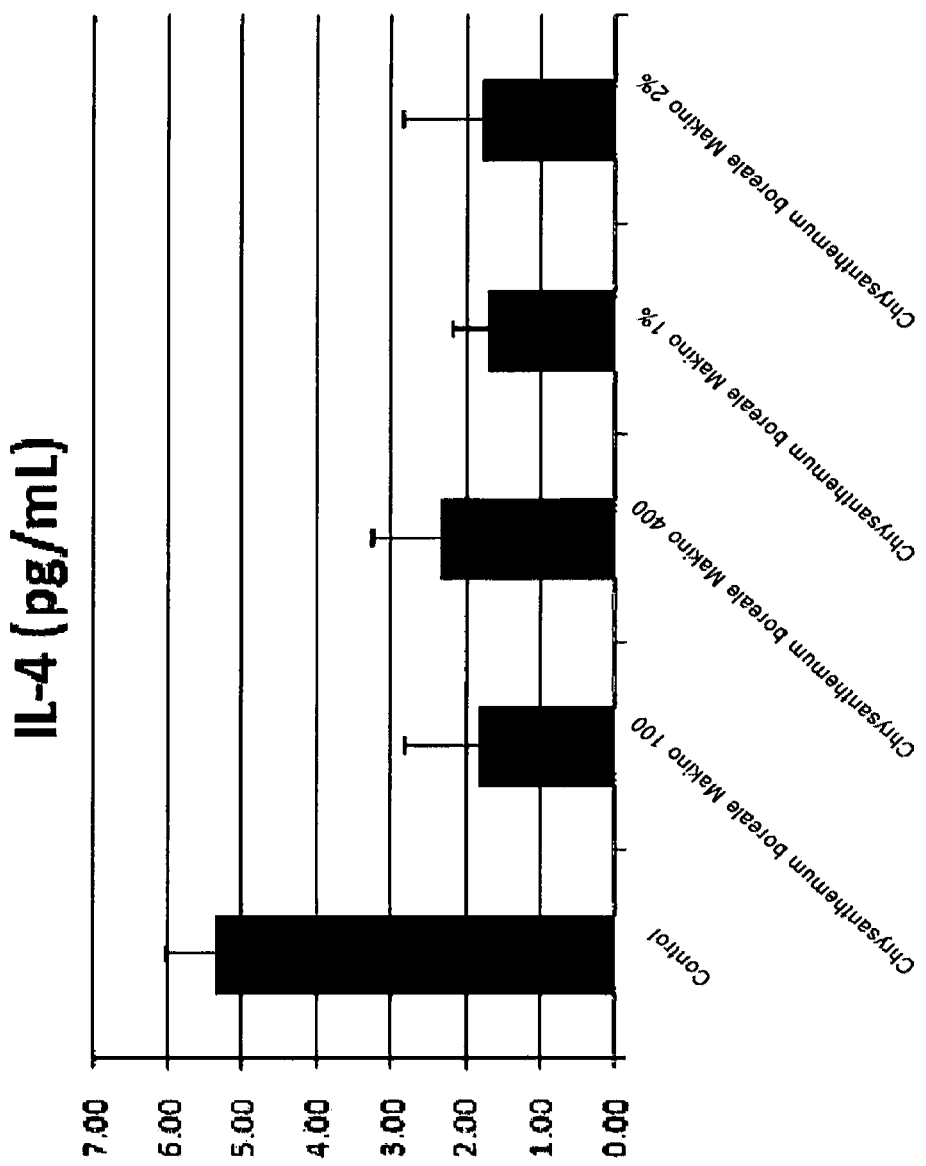
FIG. 14 shows the results of measuring serum IL-4 level of atopic dermatitis-induced NC/Nga mouse model after treatment with the extract of *Chrysanthemum boreale* Makino.

Serum IL-4 levels were 5.4±0.7 pg/ml in the control group, 1.8±1.0 pg/ml and 2.3±1.0 pg/ml in the oral administration groups (100 mg/kg and 400 mg/kg of *Chrysanthemum boreale* Makino), and 1.7±0.5 pg/ml and 1.8±1.1 pg/ml in the topical administration groups (1% and 2% *Chrysanthemum boreale* Makino), indicating a significant reduction (FIG. 14). Table 7 shows the results of determination of serum IgE, IFN-γ and IL-4 levels.

to neutrophil infiltration was scattered throughout the tissue, ear cartilage was partially broken by inflammation due to neutrophil infiltration, and neutrophil infiltration into the skin was also observed. Severe fibroblast proliferation and collagen layer hyperplasia were observed, and suppurative inflammation due to the bacteria colony was also observed (FIG. 15).

In the ear tissue photograph of the topical administration group (1% *Chrysanthemum boreale* Makino), slight hemorrhage and slight inflammation due to neutrophil infiltration into the skin were observed, and collagen layer hyperplasia were also observed, but the symptoms were ameliorated compared to those of the control group (FIG. 15).

In the ear tissue photograph of the topical administration group (2% *Chrysanthemum boreale* Makino), slight neutrophil infiltration was observed, and slight ulceration and hemorrhage were observed in some subjects, but the symptoms were ameliorated compared to those of the control group (FIG. 15).

In the ear tissue photograph of the oral administration group (100 mg/kg of *Chrysanthemum boreale* Makino), no ulceration and hemorrhage were observed, and inflammation of the skin layer and fibroblast proliferation due to collagen layer hyperplasia were observed in some subjects, but the symptoms were ameliorated compared to those of the control group (FIG. 15).

In the ear tissue photograph of the oral administration group (400 mg/kg of *Chrysanthemum boreale* Makino), ulceration and hemorrhage, and inflammation and fibroblast proliferation due to collagen layer hyperplasia were not

TABLE 7

|  | dose |  | IgE (ng/mL) |  | IL-4 (pg/mL) | IFN-γ (pg/mL) |
| --- | --- | --- | --- | --- | --- | --- |
| Normal | — | — | 77.4 ± 6.6 | 24.6 ± 6.6 | 0.0 ± 0.9 | 3.4 ± 0.5 |
| Control | — | — | 106.8 ± 13.4[##] | 61.6 ± 9.3[##] | 5.4 ± 0.7[##] | 46.7 ± 21.5[#] |
| CBP1 | 100 mg/kg | oral administration | 63.5 ± 16.9** | — | 1.8 ± 1.0** | 3.3 ± 0.4* |
| CBP4 | 400 mg/kg | oral administration | 47.6 ± 8.9** | — | 2.3 ± 1.0** | 3.5 ± 0.5* |
| CBS1 | 1% | topical administration | — | 37.2 ± 6.6** | 1.7 ± 0.5** | 3.5 ± 0.4* |
| CBS2 | 2% | topical administration | — | 46.7 ± 7.1* | 1.8 ± 1.1** | 3.6 ± 0.4* |

All the data are expressed as mean ± SD (N = 5).
[##]$p < 0.01$, comparison with normal group
*$p < 0.05$,
**$p < 0.01$, comparison with control group E. Tissue Examination The mice used in the experiments were sacrificed after the termination of the experiments, and then the ear tissues were removed and fixed in 10% formalin solution. The tissues were embedded in paraffin, and then cut to a thickness of 3-4 μm, followed by H&E (Hematoxylin & Eosin) staining. Then, ulceration, epidermal thickness of atopic dermatitis-induced tissue, mast cell infiltration, eosinophil infiltration, neutrophil and lymphocyte infiltration, and fibroblast proliferation and collagen layer hyperplasia were investigated.

In the ear tissue photograph of the normal group, ear cartilage was uniformly arranged, and the subcutaneous layer, dermis, and epidermis were all uniformly arranged, and no ulceration, hemorrhage or inflammation was observed (FIG. 15).

In the ear tissue photograph of the control group, severe ulceration and hemorrhage were observed, inflammation due observed, indicating that the symptoms were considerably ameliorated compared to those of the control group (FIG. 15).

Consequently, no ulceration was observed in the normal group, but severe ulceration was observed in the control group. No ulceration was observed in most of the oral administration groups (100 mg/kg and 400 mg/kg of *Chrysanthemum boreale* Makino) and the topical administration groups (1% and 2% *Chrysanthemum boreale* Makino).

Neutrophil and lymphocyte infiltration was not observed in the normal group, and severe neutrophil and lymphocyte infiltration was observed in the control group. Slight neutrophil and lymphocyte infiltration was observed in most of the oral administration groups (100 mg/kg and 400 mg/kg of *Chrysanthemum boreale* Makino) and the topical administration groups (1% and 2% *Chrysanthemum boreale* Makino), but the symptoms were ameliorated compared to those of the control group.

Fibroblast proliferation and collagen layer hyperplasia were not observed in the normal group, but severe fibroblast proliferation and collagen layer hyperplasia were observed in the control group. No fibroblast proliferation and collagen layer hyperplasia were observed in the oral administration group (400 mg/kg of *Chrysanthemum boreale* Makino) and the topical administration group (2% *Chrysanthemum boreale* Makino), but various stages of fibroblast proliferation and collagen layer hyperplasia were observed in some subjects of the oral administration group (100 mg/kg of *Chrysanthemum boreale* Makino) and the topical administration group (1% *Chrysanthemum boreale* Makino), but the symptoms were ameliorated compared to those of the control group.

Further, when the number of mast cells visualized under a microscope with 400× magnification was counted, 2.35 mast cells were observed in the normal group and 7.65 in atopic dermatitis-induced group, indicating an increase in the number of mast cells in the control group. 8.5 mast cells were observed in the topical administration group (1% *Chrysanthemum boreale* Makino), 8.85 mast cells in the topical administration group (2% *Chrysanthemum boreale* Makino), 7.15 mast cells in the oral administration group (100 mg/kg of *Chrysanthemum boreale* Makino), and 6.265 mast cells in the oral administration group (400 mg/kg of *Chrysanthemum boreale* Makino), indicating that the number of mast cells was ameliorated in the oral administration group (400 mg/kg of *Chrysanthemum boreale* Makino) than in the control group.

Example 3

Measurement of Cellular Inflammatory Factors 3-1. Experimental Method
(1) Experimental Method
A. Cell Culture In the present experiment, murine macrophage RAW 264.7 cell line was obtained from the Korean Cell Line Bank (Korea) to perform the experiments. RAW 264.7 cells were grown in DMEM. RAW 264.7 cells were inoculated into a T-flask at a density of 2×105 cells/ml and cultured in a humidified CO2 incubator (5% CO2, 95% air) at 37° C. for 24 hrs. Subsequently, the cells were treated with LPS (10 μg/ml) diluted in media without FBS for 24 hrs, and treated again with the drug (1 mg/ml) diluted in media without FBS. After 24 hrs, the cells were used for the experiments.

B. Nitrite Determination

The activity of induced nitric oxide synthase (iNOS) was measured by determination of NO (nitric oxide) production. For the determination of NO production in Raw 264.7 cells, a Nitrate/Nitrite colorimetric assay kit was used to measure cytoplasmic $NO^{2-}$. The experiment was performed using a Griess reagent in accordance with the manufacturer's instructions (Cayman Chemical Company).

C. Western blot analysis of iNOS (induced nitric oxide synthase) expression

Western blotting was performed to confirm effects of the extracts and fractions of *Chrysanthemum boreale* Makino on the iNOS (induced nitric oxide synthase) expression in Raw 264.7 cells.

Cells treated with the extracts and fractions of *Chrysanthemum boreale* and control group were harvested, and washed with PBS twice. 100 μl of Pro-prep™ (Intron, Korea) reagent was added thereto, and left at −20° C. for 10 min. Subsequently, centrifugation was performed at 4° C., 12,000 rpm for 10 min to obtain the supernatant. The obtained protein solution was quantified using Pro-measure™ (Intron, Korea) solution, and 50 μg of protein was mixed with the sample buffer. The mixture was heated at 95° C. for 5 min, and then stored at −20° C. The prepared sample was electrophoresed on a 12% SDS-acrylamide gel, and then transferred onto PVDF membrane. Thereafter, the membrane was blocked in 5% skim milk at room temperature for 1 hr, and incubated at 4° C. overnight with iNOS primary antibody that was diluted in 5% skim milk to a predetermined ratio. Next day, the membrane was washed with TBST for 5 min three times, and then incubated with anti-mouse secondary antibody at room temperature for 1 hr. Then, the membrane was washed with TBST for 10 min three times, and reacted with ECL Western Substrate (PIERCE, #3216) solution for 1 min, followed by development of X-ray film (Kodak).

D. Western Blot Analysis of COX-2 Inhibition

To examine the effect of the extracts and fractions of *Chrysanthemum boreale* Makino on the expression of COX-2 which produces PGE2, Western blot analysis was performed. The cells treated with the extract of *Chrysanthemum boreale* Makino and control group were harvested and washed with PBS twice. 100 μl of Pro-prep™ reagent was added thereto, and left at −20° C. for 10 min. Subsequently, centrifugation was performed at 4° C., 12,000 rpm for 10 min to obtain the supernatant. The obtained protein solution was quantified using Pro-measure™ solution, and 50 μg of protein was mixed with the sample buffer. The mixture was heated at 95° C. for 5 min, and then stored at −20° C. The prepared sample was electrophoresed on a 12% SDS-acrylamide gel, and then transferred onto PVDF membrane. Thereafter, the membrane was blocked in 5% skim milk at room temperature for 1 hr, and incubated at 4° C. overnight with COX-2 primary antibody that was diluted in 5% skim milk to a predetermined ratio. The next day, the membrane was washed with TBST for 5 min three times, and then incubated with anti-mouse and goat secondary antibody at room temperature for 1 hr. Then, the membrane was washed with TBST for 10 min three times, and reacted with ECL Western Substrate (PIERCE, #3216) solution for 1 min, followed by development of the x-ray film (Kodak).

E. Determination of PGE2 Production

To examine the COX-2 activity by the extracts and fractions of *Chrysanthemum boreale* Makino, intracellular PGE2 level was determined. The experiment was performed in the same manner as in NO assay, and a cytoplasmic solution was taken to examine the level of PGE2 release in accordance with the protocol of PGE2 EIA system (Amersham, RPN222).

F. IκB Phosphorylation and Degradation (Western Blot)

To examine the effect of the extracts and fractions of *Chrysanthemum boreale* Makino on LPS-induced IκB phosphorylation and degradation, Western blot analysis was performed.

Each sample-treated cells and control group were harvested and washed with PBS twice. 100 μl of Pro-prep™ reagent was added thereto, and left at −20° C. for 10 min. Subsequently, centrifugation was performed at 4° C., 12,000 rpm for 10 min to obtain the supernatant. The obtained protein solution was quantified using Pro-measure™ solution (Intron), and 50 μg of protein was mixed with the sample buffer. The mixture was heated at 95° C. for 5 min, and then stored at −20° C. The prepared sample was electrophoresed on a 12% SDS-acrylamide gel, and then transferred onto PVDF membrane. Thereafter, the membrane was blocked in 5% skim milk at room temperature for 1 hr, and incubated at 4° C. overnight with IκBα primary antibody that was diluted in 5% skim milk to a predetermined ratio. The next day, the membrane was washed with TBST for 5 min three times, and incubated with anti-mouse secondary antibody at room temperature for 1 hr. Then, the membrane was washed with TBST for 10 min three times, followed by color development with BCIP-NBT solution (Nakanai Tesque, Japan).

G. Cytoplasmic and Nuclear NF-κB Expression

To examine the effect of the extracts and fractions of *Chrysanthemum boreale* Makino on LPS-induced NF-κB nuclear translocation, cytoplasmic and nuclear NF-κB were separated (p50, p65) to perform Western blot analysis.

Each sample-treated experimental group and control group were harvested and washed with PBS twice. 0.4 ml of cell lysis buffer (10 mM HEPES (pH 7.9), 10 mM KCl, 0.1 mM EDTA, 0.1 mM EGTA, 1 mM DTT, 0.5 mM PMSF, 2.0 μg/μl aprotinin) was added thereto, and left at 4° C. for 15 min. Then, 25 μl of 10% NP40 was added thereto, and vigorously mixed on a voltex for 10 sec. The reactant was centrifuged at 4° C., 1,300 rpm for 2 min to obtain the supernatant containing cytoplasmic protein. 50 μl of ice-cold nuclear extraction buffer) (containing 20 mM HEPES (pH 7.9), 0.4M NaCl, 1 mM EDTA, 1 mM EGTA, 1 mM DTT, 1 mM PMSF, 2.0 μg/μl leupeptin, and 2.0 μg/μl aprotinin) was added to the pellets, and incubated for 15 min at 4° C. with intermittent mixing. Then, the sample was centrifuged at 4° C., 1,300 rpm for 2 min to obtain the nuclear protein supernatant. The obtained cytoplasmic and nuclear solutions were quantified using Pro-measure™ solution, and 30 μg of protein was mixed with the sample buffer. The mixture was heated at 95° C. for 5 min, and then stored at −20° C. The prepared sample was electrophoresed on a 12% SDS-acrylamide gel, and then transferred onto PVDF membrane. Thereafter, the membrane was blocked in 5% skim milk at room temperature for 1 hr, and incubated at 4° C. overnight with NF-κB p65 primary antibody that was diluted in 5% skim milk to a predetermined ratio. Next day, the membrane was washed with TBST for 5 min three times, and then incubated with anti-mouse secondary antibody at room temperature for 1 hr. Then, the membrane was washed with TBST for 10 min three times, followed by color development with BCIP-NBT solution (Nakanai Tesque, Japan).

(2) Reagents and Instruments

DMEM medium (Gibco BRL Co., U.S.A.)
RPMI 1604 medium (Gibco BRL Co., U.S.A.)
Fetal bovine serum (FBS, Gibco BRL Co., U.S.A.)
penicillin (Gibco BRL Co., U.S.A.)
streptomycin (Gibco BRL Co., U.S.A.)
Nitrate/Nitrite Colorimetric assay kit (Cayman Chemical Co., U.S.A.)
Lipopolysaccharide (Sigma Co., U.S.A.)
Pro-prep™ protein extraction solution (Intron Biotechnology Co., Korea)
Pro-measure™ protein measurement solution (Intron Biotechnology Co., Korea)
COX-2 monoclonal antibody (Santa Cruz Biotechnology Co., U.S.A.)
Anti-goat antibody (Zymed Co., U.S.A.)
methanol (MeOH) (Duksan Chemical Co., Korea)
chloroform (Duksan Chemical Co., Korea)
ELISA reader: Versamax (Molecular Devices Co., U.S.A.)
FT-03 (Grass, U.S.A.)

3-2. Experimental Results

A. Results of Nitrite Measurement

Figure 16:
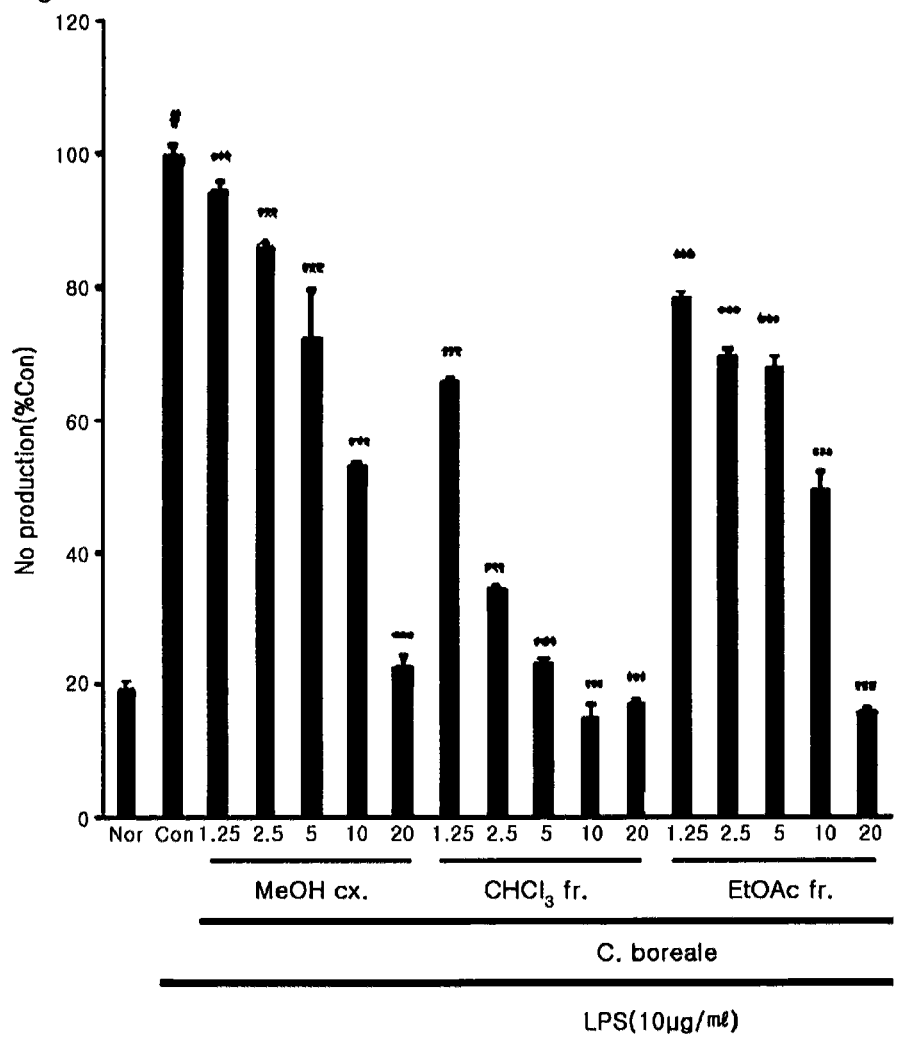
FIG. 16 shows LPS-induced intracellular nitric oxide production in RAW 264.7 cells after treatment with the fractions of *Chrysanthemum boreale* Makino.

To measure LPS-induced NO production in RAW 264.7 cells, cytoplasmic nitrite was measured using a Nitrate/Nitrite Colorimetric assay kit. The experiment was performed using a Griess reagent in accordance with the manufacturer's instructions (Cayman Chemical Company). As a result, each nitrite production was reduced to approximately 38%, 78%, and 30% in the methanol (MeOH) extract, chloroform (CHCl3) fraction, and ethyl acetate (EtOAc) fraction at the concentration of 5 μg/ml, as compared to the control group (FIG. 16). Table 8 shows the effects of the extracts and fractions of *Chrysanthemum boreale* Makino on LPS-induced NO production in RAW 264.7 cells.

TABLE 8

| sample | concentration (μg/ml) | production (%) |
|---|---|---|
| normal group | | 16.7 ± 0.2 |
| control group | | 100.0 ± 1.5 |
| MeOH extract | 1.25 | 83.1 ± 0.6 |
| | 2.5 | 82.3 ± 0.3 |
| | 5 | 62.1 ± 0.5 |
| | 10 | 52.0 ± 1.1 |
| | 20 | 21.8 ± 0.2 |
| CHCl$_3$ fraction | 1.25 | 49.2 ± 0.4 |
| | 2.5 | 34.5 ± 0.2 |
| | 5 | 21.8 ± 0.6 |
| | 10 | 11.7 ± 0.0 |
| | 20 | 13.8 ± 0.3 |
| EtOAc fraction | 1.25 | 73.6 ± 0.8 |
| | 2.5 | 73.9 ± 1.1 |
| | 5 | 69.8 ± 0.7 |
| | 10 | 49.7 ± 3.0 |
| | 20 | 15.6 ± 0.3 |

B. Western Blot Analysis of iNOS (Induced Nitric Oxide Synthase) Expression

Figure 17:
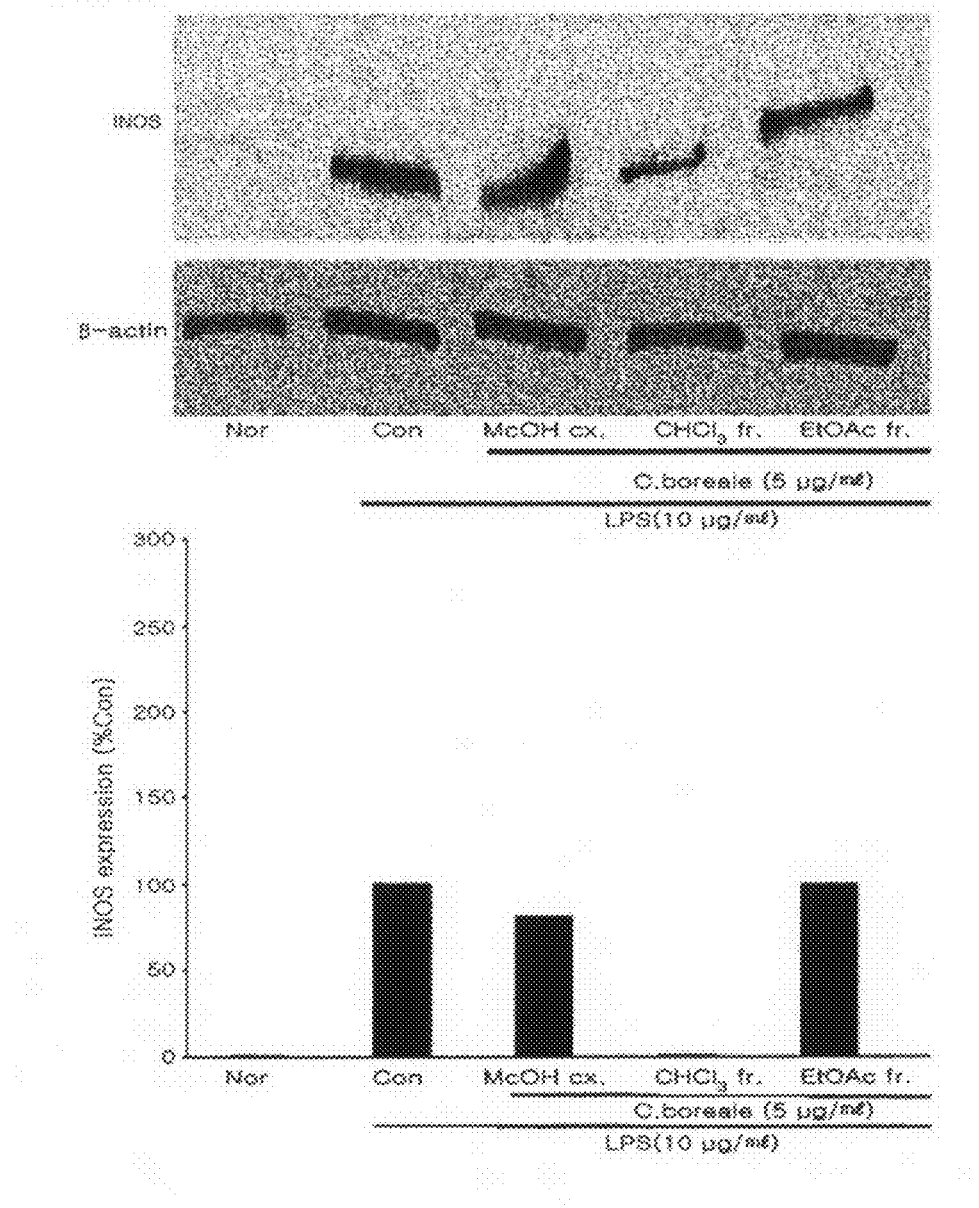
FIG. 17 shows LPS-induced intracellular iNOS (induced nitric oxide synthase) production in RAW 264.7 cells after treatment with the fractions of *Chrysanthemum boreale* Makino.

The effects of *Chrysanthemum boreale* Makino on iNOS (induced nitric oxide synthase) expression in RAW 264.7 cells was confirmed by Western blot analysis. As a result, each iNOS (induced nitric oxide synthase) expression was reduced to approximately 19%, 98%, and 0.5% in the methanol (MeOH) extract, chloroform (CHCl3) fraction, and ethyl acetate (EtOAc) fraction, as compared to the control group (FIG. 17). Table 9 shows the effects of the extracts and fractions of *Chrysanthemum boreale* Makino on LPS-induced iNOS (induced nitric oxide synthase) expression in RAW 264.7 cells.

TABLE 9

| sample | sample concentration (μg/ml) | expression level (%/Con) |
|---|---|---|
| normal group | | 1.0 |
| control group | | 100.0 |
| MeOH extract | 5 | 80.7 |
| CHCl$_3$ fraction | 5 | 1.9 |
| EtOAc fraction | 5 | 99.5 |

C. Results of PGE2 Measurement

Figure 18:
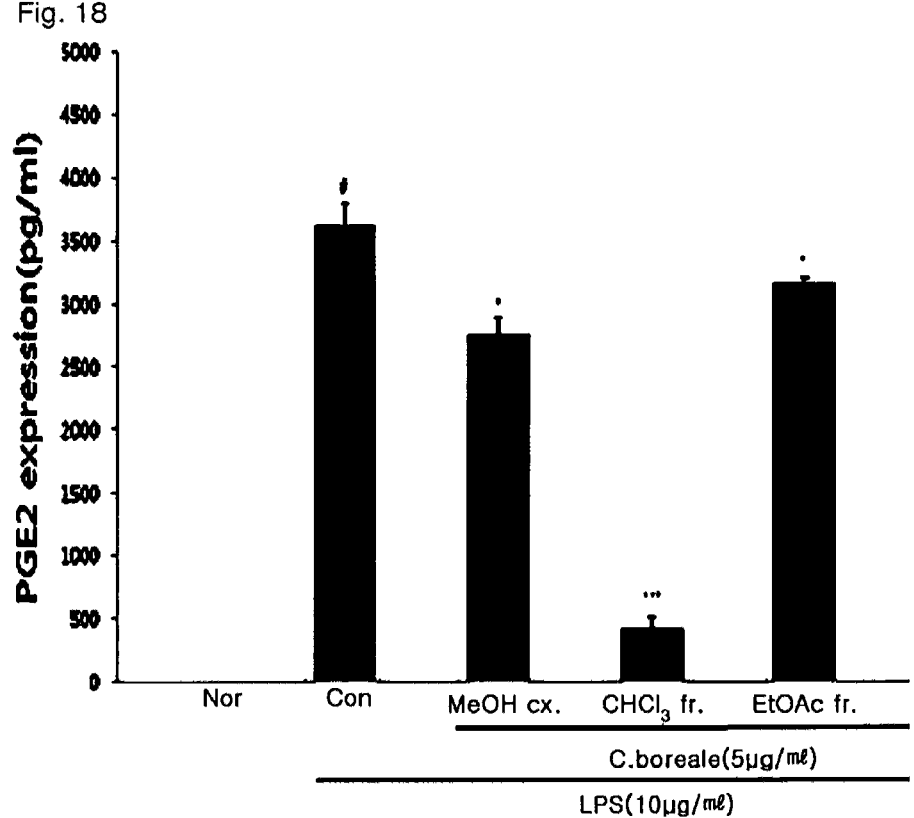
FIG. 18 shows LPS-induced intracellular PGE2 production in RAW 264.7 cells after treatment with the fractions of *Chrysanthemum boreale* Makino.

To examine the COX-2 activity by the extracts of *Chrysanthemum boreale* Makino, intracellular PGE2 level was determined. As a result, each PGE2 production was reduced to approximately 24%, 88%, and 10% in the methanol extract, chloroform (CHCl3) fraction, and ethyl acetate (EtOAc) fraction, as compared to the control group (FIG. 18). Table 10 shows the effects of the extracts and fractions of *Chrysanthemum boreale* Makino on LPS-induced PGE2 expression in RAW 264.7 cells.

TABLE 10

| sample | sample concentration (μg/ml) | PGE$_2$ expression level (pg/ml) |
|---|---|---|
| normal group | | 1.0 ± 1.2 |
| control group | | 3603.9 ± 180.6 |
| MeOH extract | 5 | 2750.0 ± 130.9 |

TABLE 10-continued

| sample | sample concentration (μg/ml) | PGE$_2$ expression level (pg/ml) |
|---|---|---|
| CHCl$_3$ fraction | 5 | 423.3 ± 86.3 |
| EtOAc fraction | 5 | 3167.3 ± 41.2 |

D. Western Blot Analysis of COX-2 Expression

Figure 19:
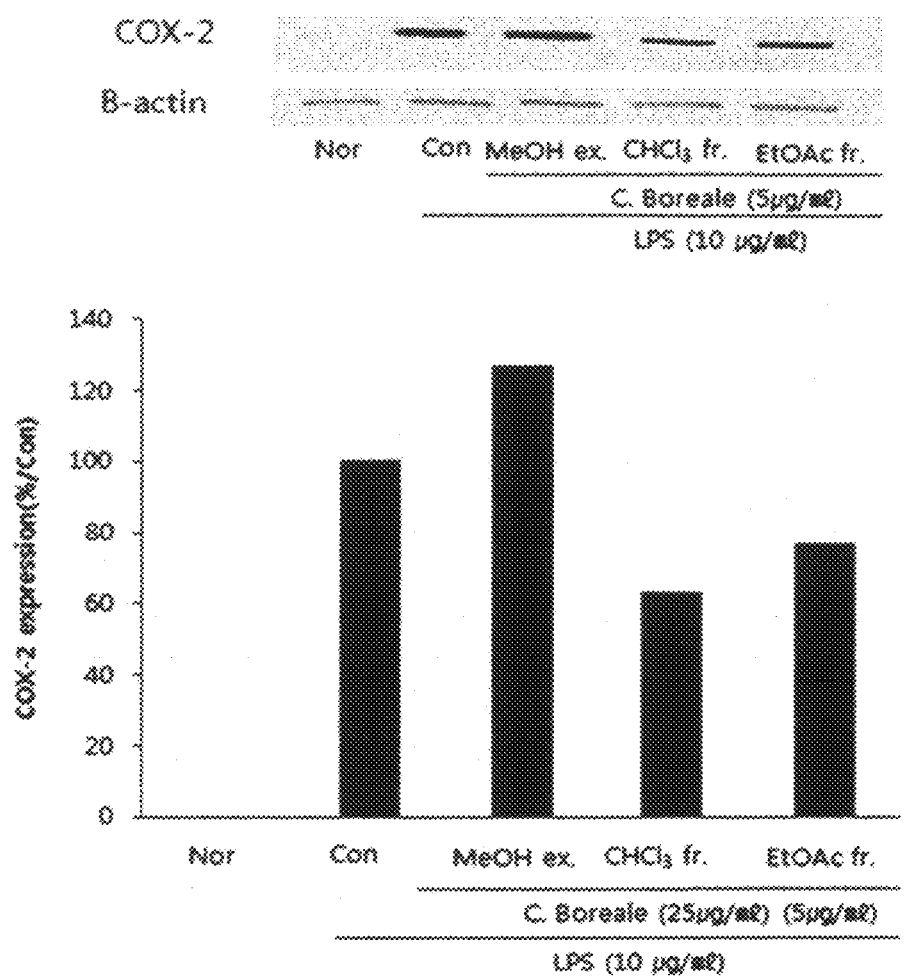
FIG. 19 shows LPS-induced intracellular COX-2 production in RAW 264.7 cells after treatment with the fractions of *Chrysanthemum boreale* Makino.

The effects of *Chrysanthemum boreale* Makino on COX-2 expression in RAW 264.7 cells was confirmed by Western blot analysis. As a result, as compared to the control group, each COX-2 expression was reduced to approximately 37% and 23% in CHCl3 fraction and EtOAc fraction, but increased to approximately 26% in the MeOH extract (FIG. 19). Table 11 shows the effects of the extracts and fractions of *Chrysanthemum boreale* Makino on LPS-induced COX-2 expression in RAW 264.7 cells.

TABLE 11

| sample | sample concentration (μg/ml) | COX-2 expression level (%/Con) |
|---|---|---|
| normal group | | 0.3 |
| control group | | 100.0 |
| MeOH extract | 5 | 126.1 |
| CHCl$_3$ fraction | 5 | 62.9 |
| EtOAc fraction | 5 | 76.9 |

E. Western Blot Analysis of IκB Expression

Figure 20:
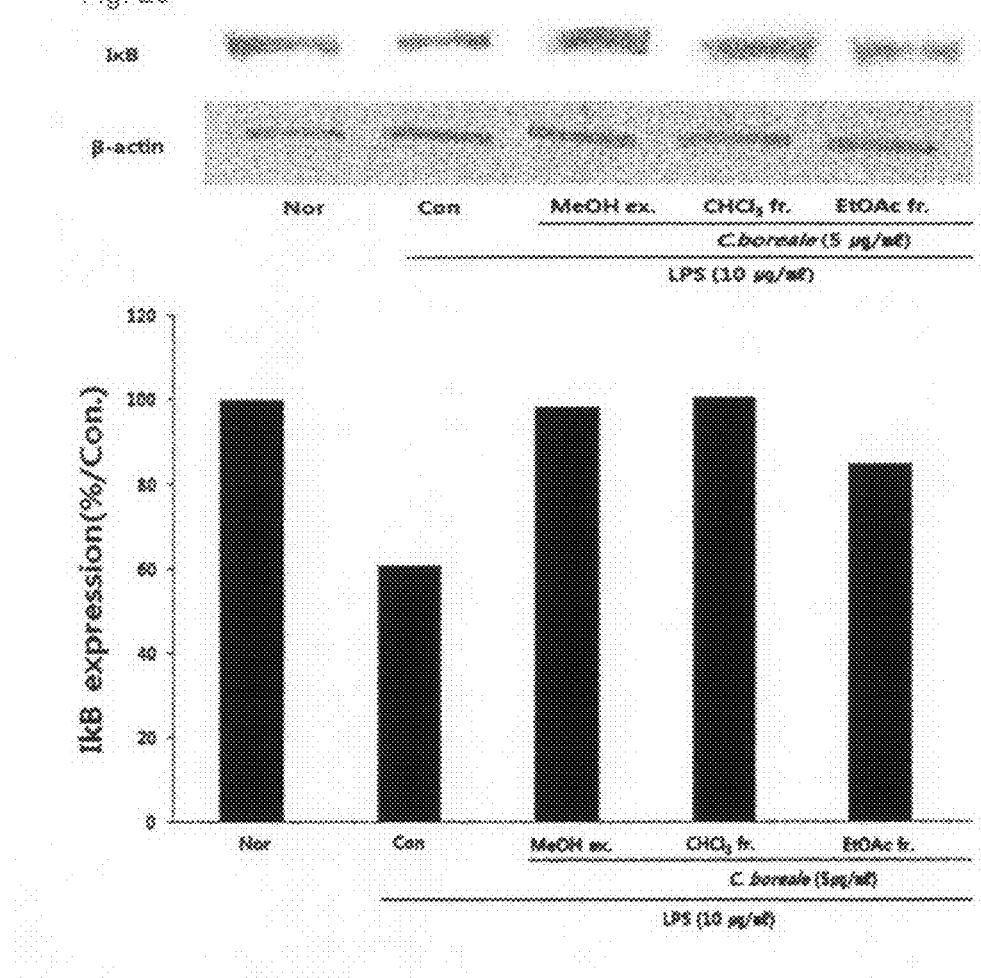
FIG. 20 shows LPS-induced intracellular IκB production in RAW 264.7 cells after treatment with the fractions of *Chrysanthemum boreale* Makino.
Figure 21:
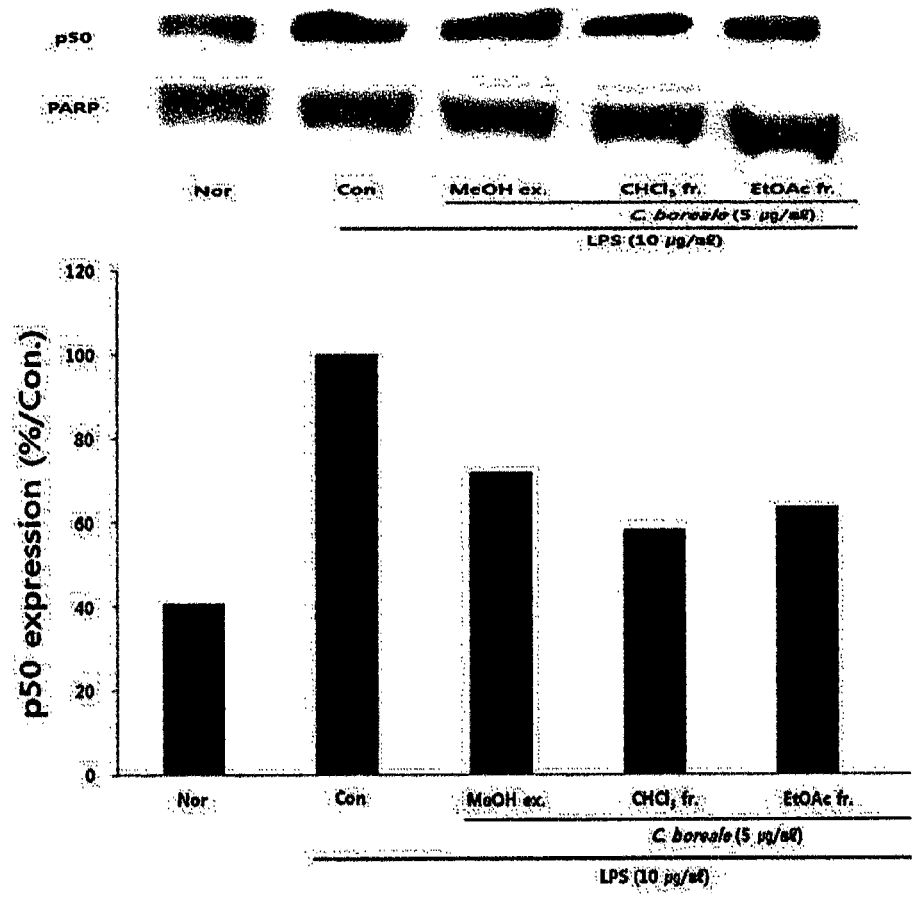
FIG. 21 shows LPS-induced intracellular P50 production in RAW 264.7 cells after treatment with the fractions of *Chrysanthemum boreale* Makino.

To examine the P50/P65 activity by the extracts of *Chrysanthemum boreale* Makino, the level of P50/P65 inhibitor, IκB was determined. As a result, the level was reduced to approximately 61%, 65%, and 39.6% in the MeOH extract, CHCl3 fraction, and EtOAc fraction, as compared to the control group (FIG. 20). Table 12 shows the effects of the extracts and fractions of *Chrysanthemum boreale* Makino on LPS-induced IκB expression in RAW 264.7 cells.

TABLE 12

| sample | sample concentration (μg/ml) | IκB expression level (%/Con) |
|---|---|---|
| normal group | | 100.0 |
| control group | | 60.8 |
| MeOH extract | 5 | 98.1 |
| CHCl$_3$ fraction | 5 | 100.6 |
| EtOAc fraction | 5 | 84.9 |

F. Western Blot Analysis of NF-κB (P50, P65) Expression

Figure 22:
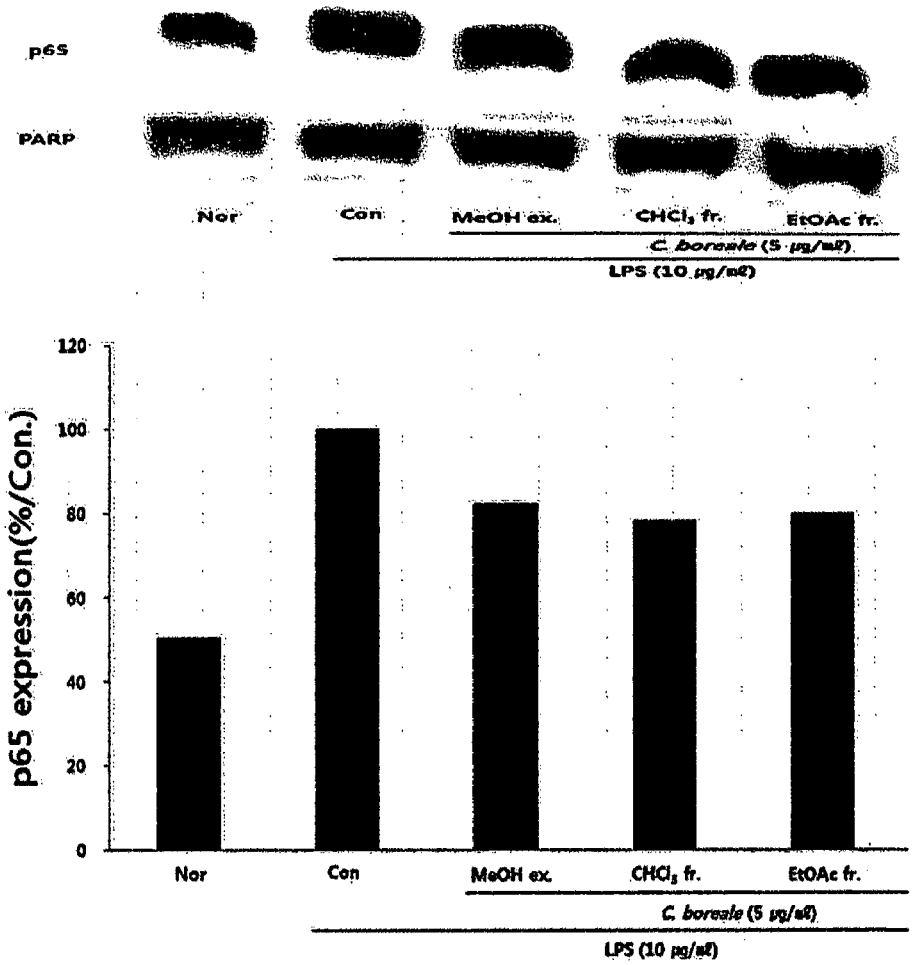
FIG. 22 shows LPS-induced intracellular P65 production in RAW 264.7 cells after treatment with the fractions of *Chrysanthemum boreale* Makino.

The effects of *Chrysanthemum boreale* Makino on P50/P65 activity were confirmed. As a result, the P50 expression was reduced to approximately 28%, 42%, and 36% in the MeOH extract, CHCl3 fraction, and EtOAc fraction, as compared to the control group (FIG. 21), and the P65 expression was reduced to approximately 18%, 22%, and 20% in the MeOH extract, CHCl3 fraction, and EtOAc fraction, as compared to the control group (FIG. 22). Table 13 shows the effects of the extracts and fractions of *Chrysanthemum boreale* Makino on LPS-induced NF-κB (P50, P65) expression in RAW 264.7 cells.

TABLE 13

| sample | sample concentration (μg/ml) | p50 expression (%/Con) | p65 expression level (%/Con) |
|---|---|---|---|
| normal group | | 40.9 | 50.7 |
| control group | | 100.0 | 100.0 |
| MeOH extract | 5 | 72.2 | 82.4 |
| CHCl$_3$ fraction | 5 | 58.5 | 78.4 |
| EtOAc fraction | 5 | 63.8 | 80.3 |

3-3. Comparative Example- *Chrysanthemi Indici. Flos*
(1) Sample Extraction
1) Material

*Chrysanthemi Indici Flos* (scientific name) used in the present experiment is a Korean chamomile, also called snow chamomile, golden chamomile, or yellow chamomile, and cultivated in youngchun, the North Kyungsang Province, and collected on Oct. 3, 2007. A part of the medicinal herb was stored at Dept. of Herbology, College of Oriental Medicine, Kyung Hee University.

2) Sample Extraction and Fractionation
① Sample Extraction 100 g of *Chrysanthemi Indici Flos* was extracted using 100% methanol (MeOH) as a solvent in a 110° C. extractor three times, and concentrated under reduced pressure using a rotary evaporator to obtain 32.5 g of 100% methanol extract.

② Fractionation 32.5 g of the methanol extract of *Chrysanthemi Indici Flos* was dissolved in distilled water, and then fractionated using chloroform (CHCl3) to obtain 12.9 g of water (H2O) fraction and 2.9 g of chloroform fraction.

3) Reagents and Instruments

DMEM medium (Hyclone, U.S.A.)
Fetal bovine serum (FBS, Gibco BRL Co., U.S.A.)
Penicillin (Gibco BRL Co., U.S.A.)
Streptomycin (Gibco BRL Co., U.S.A.)
Cell Titer 96 (Promega Co., U.S.A.)
Nitrate/Nitrite Colorimetric assay kit (Cayman Chemical Co., U.S.A.)
Lipopolysaccharide (Sigma Co., U.S.A.)
Pro-prep™ protein extraction solution (Intron Biotechnology Co., Korea)
Pro-measure™ protein measurement solution (Intron Biotechnology Co., Korea)
COX-2 monoclonal antibody (BD Bioscience Pharmingen Co., U.S.A.)
iNOS monoclonal antibody (BD Bioscience Pharmingen Co., U.S.A.)
Anti-mouse antibody (cell Signalling Co., U.S.A.)
Prostaglandin E2 biotrak ELISA system (BD Bioscience Pharmingen Co., U.S.A.)
ECL Western Substrate (PIERCE, #3216, Rockford, U.S.A)
RayBio mouse Inflammation Antibody Array I (AAM-INF-1-8, RayBiotech, Norcross, Ga., U.S.A.)
ELISA reader: Versamax (Molecular Devices Co., U.S.A.)
UV/VIS Spectrophotometer (Gilson Co., U.S.A.)

(2) Experimental Method
1) Nitrite Determination

The activity of induced nitric oxide synthase (iNOS) was measured by determination of NO (nitric oxide) production. For the determination of NO production in Raw 264.7 cells, a Nitrate/Nitrite colorimetric assay kit was used to measure cytoplasmic nitric oxide. The experiment was performed in accordance with the manufacturer's instructions (Cayman Chemical Company). All the values are expressed as mean±SD (standard deviation). A student T-test was used to determine significance. All experiments were repeated three times.

2) Determination of iNOS Expression

Western blotting was performed to confirm the effects of the extracts and fractions of *Chrysanthemi Indici Flos* on the expression of iNOS, which is an enzyme inducing NO production.

Cells treated with the extracts of *Chrysanthemi Indici Flos* and a control group were harvested, and washed with PBS twice. 100 µl of Pro-prep™ (Intron, Korea) reagent was added thereto, and left at −20° C. for 10 min. Subsequently, centrifugation was performed at 4° C., 12,000 rpm for 10 min to obtain the supernatant. The obtained protein solution was quantified using Pro-measure™ (Intron, Korea) solution, and 50 µg of protein was mixed with the sample buffer. The mixture was heated at 95° C. for 5 min, and then stored at −20° C. The prepared sample was electrophoresed on a 12% SDS-acrylamide gel, and then transferred onto PVDF membrane. Thereafter, the membrane was blocked in 5% skim milk at room temperature for 1 hr, and incubated at 4° C. overnight with iNOS primary antibody that was diluted in 5% skim milk to a predetermined ratio. The next day, the membrane was washed with TBST for 5 min three times, and then incubated with anti-mouse secondary antibody at room temperature for 1 hr. Then, the membrane was washed with TBST for 10 min three times, and reacted with ECL Western Substrate (PIERCE, #3216) solution for 1 min, followed by development of X-ray film (Kodak).

3) Determination of PGE2 Production

To examine the COX-2 activity by the extracts and fractions of *Chrysanthemi Indici. Flos*, intracellular PGE2 (prostaglandin E2) level was determined. The experiment was performed in the same manner as in NO assay, and a cytoplasmic solution was taken to examine the level of PGE2 release in accordance with the protocol of Prostaglandin E2 Enzyme immunoassay Biotrak (EIA) system (Amersham, RPN222).

4) Determination of COX-2 Expression

To examine the effect of the extracts and fractions of *Chrysanthemi Indici Flos* on the expression of COX-2 which produces PGE2, Western blot analysis was performed.

Each sample-treated cells and control group were harvested and washed with PBS twice. 100 µl of Pro-prep™ reagent was added thereto, and left at −20° C. for 10 min. Subsequently, centrifugation was performed at 4° C., 12,000 rpm for 10 min to obtain the supernatant. The obtained protein solution was quantified using Pro-measure™ solution, and 50 µg of protein was mixed with the sample buffer. The mixture was heated at 95° C. for 5 min, and then stored at −20° C. The prepared sample was electrophoresed on a 12% SDS-acrylamide gel, and then transferred onto PVDF membrane. Thereafter, the membrane was blocked in 5% skim milk at room temperature for 1 hr, and incubated at 4° C. overnight with COX-2 primary antibody that was diluted in 5% skim milk to a predetermined ratio. Next day, the membrane was washed with TBST for 5 min three times, and then incubated with anti-mouse secondary antibody at room temperature for 1 hr. Then, the membrane was washed with TBST for 10 min three times, and reacted with ECL Western Substrate (PIERCE, #3216) solution for 1 min, followed by development of X-ray film (Kodak).

5) Determination of IκB Phosphorylation and Degradation

To examine the effect of the extracts and fractions of *Chrysanthemi Indici Flos* on LPS-induced IκB phosphorylation and degradation, Western blot analysis was performed.

Each sample-treated cell group and control group were harvested and washed with PBS twice. 100 µl of Pro-prep™ reagent was added thereto, and left at −20° C. for 10 min. Subsequently, centrifugation was performed at 4° C., 12,000 rpm for 10 min to obtain the supernatant. The obtained protein solution was quantified using Promeasure™ solution (Intron), and 50 µg of protein was mixed with the sample buffer. The mixture was heated at 95° C. for 5 min, and then stored at −20° C. The prepared sample was electrophoresed on a 12% SDS-acrylamide gel, and then transferred onto PVDF membrane. Thereafter, the membrane was blocked in 5% skim milk at room temperature for 1 hr, and incubated at 4° C. overnight with IκBα primary antibody that was diluted in 5% skim milk to a predetermined ratio. Next day, the membrane was washed with TBST for 5 min three times, and then incubated with anti-mouse secondary antibody at room temperature for 1 hr. Then, the membrane was washed with TBST for 10 min three times, followed by color development with BCIP-NBT solution (Nakanai Tesque, Japan).

6) Determination of Cytoplasmic and Nuclear NF-κB Expression

To examine the effect of the extracts and fractions of *Chrysanthemi Indici Flos* on LPS-induced NF-κB nuclear translocation, cytoplasmic and nuclear proteins were separated to perform Western blot analysis.

Each sample-treated experimental group and control group were harvested and washed with PBS twice. 0.4 me of cell lysis buffer (10 mM HEPES (pH 7.9), 10 mM KCl, 0.1 mM EDTA, 0.1 mM EGTA, 1 mM DTT, 0.5 mM PMSF, 2.0 µg/µl aprotinin) was added thereto, and left at 4° C. for 15 min. Then, 25 µl of 10% NP40 was added thereto, and vigorously mixed on a voltex for 10 sec. The reactant was centrifuged at 4° C., 1,300 rpm for 2 min to obtain the supernatant containing cytoplasmic protein. 50 µl of ice-cold nuclear extraction buffer) (containing 20 mM HEPES (pH 7.9), 0.4M NaCl, 1 mM EDTA, 1 mM EGTA, 1 mM DTT, 1 mM PMSF, 2.0 µg/µl leupeptin, and 2.0 µg/µl aprotinin) was added to the pellets, and incubated for 15 min at 4° C. with intermittent mixing. Then, the sample was centrifuged at 4° C., 1,300 rpm for 2 min to obtain the nuclear protein supernatant. The obtained cytoplasmic and nuclear solutions were quantified using Promeasure™ solution, and 30 µg of protein was mixed with the sample buffer. The mixture was heated at 95° C. for 5 min, and then stored at −20° C. The prepared sample was electrophoresed on a 12% SDS-acrylamide gel, and then transferred onto PVDF membrane. Thereafter, the membrane was blocked in 5% skim milk at room temperature for 1 hr, and incubated at 4° C. overnight with NF-κB p65 primary antibody that was diluted in 5% skim milk to a predetermined ratio. Next day, the membrane was washed with TBST for 5 min three times, and then incubated with anti-mouse secondary antibody at room temperature for 1 hr. Then, the membrane was washed with TBST for 10 min three times, followed by color development with BCIP-NBT solution (Nakanai Tesque, Japan).

(3) Experimental Results

1) Result of Nitrite Determination

Figure 23:
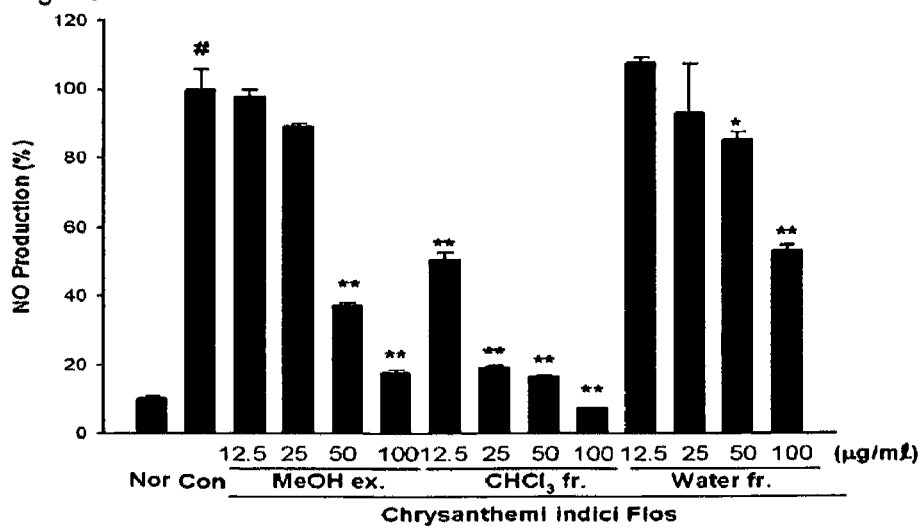
FIG. 23 shows LPS-induced intracellular nitric oxide production in RAW 264.7 cells after treatment with the fractions of *Chrysanthemi Indici Flos;*

As a result of determining nitrite expression, each nitrite production was 97.9%, 89.0%, 37.3%, and 17.8% in the methanol extract and 50.6%, 19.2%, 16.6%, and 7.5% in the chloroform fraction at the sample concentrations of 12.5 µg/ml, 25 µg/ml, 50 µg/ml, and 100 µg/ml, as compared to the control group. That is, it can be seen that nitrite expression was inhibited to 50% or more at the methanol fraction of 50 µg/ml or more, and at the chloroform fraction of 25 µg/ml or more. Table 14 shows the effects of the extracts and fractions of *Chrysanthemi Indici Flos* on LPS-induced nitrite production in RAW 264.7 cells (FIG. 23).

TABLE 14

| sample | sample concentration (μg/ml) | NO production (%) |
|---|---|---|
| normal group | | 10.3 ± 0.7 |
| control group | | 100.0 ± 5.7# |
| MeOH extract | 12.5 | 97.9 ± 1.9 |
| | 25 | 89.0 ± 0.9 |
| | 50 | 37.3 ± 1.0** |
| | 100 | 17.8 ± 0.8** |
| CHCl3 fraction | 12.5 | 50.6 ± 2.1** |
| | 25 | 19.2 ± 0.5** |
| | 50 | 16.6 ± 0.5** |
| | 100 | 7.5 ± 0.1** |
| Water fraction | 12.5 | 107.6 ± 1.5 |
| | 25 | 92.8 ± 14.5 |
| | 50 | 85.2 ± 2.3* |
| | 100 | 53.2 ± 1.5** | p < 0.05, comparison with normal group
*p < 0.05,
**p < 0.01, comparison with control group
All the data are expressed as mean ± SD (N = 3).

Taken together, the extract of *Chrysanthemi Indici Flos* inhibited the nitrite production to 50% or more at the methanol extract of 50 μg/ml or more, and at the chloroform fraction of 25 μg/ml or more, but the extract of *Chrysanthemum boreale* Makino (Example 3-2) inhibited the nitrite production to 50% or more at the methanol extract of 10 μg/ml or more, at the chloroform fraction of 1.25 μg/ml or more, and at the ethyl acetate fraction of 10 μg/ml or more, indicating that much smaller amount of the extracts and fractions of *Chrysanthemum boreale* Makino showed the inhibitory effect on nitrite production that is equivalent to or higher than those of *Chrysanthemi Indici. Flos.*

2) Result of iNOS Determination

With reference to cytotoxicity and nitrite production results of the extracts and fractions of Chrysanthemi Indici. Flos, iNOS expression was determined at the concentration of 25 μg/ml. The iNOS expression was confirmed in RAW 264.7 cells by Western blotting.

Each iNOS expression was 74.9% and 0.0% in the methanol extract and chloroform fraction, showing each reduction ratio of 25.1% and 100.0%, and 69.7% in the water fraction, showing the reduction ratio of 30.3% (FIG. 24). Table 15 shows the effects of the extracts and fractions of *Chrysanthemi Indici Flos* on LPS-induced iNOS expression in RAW 264.7 cells.

TABLE 15

| sample | concentration (μg/ml) | iNOS xpression level (%/Con) |
|---|---|---|
| normal group | | 0.1 |
| control group | | 100.0 |
| MeOH extract | 25 | 74.9 |
| CHCl3 fraction | 25 | 0.0 |
| Water fraction | 25 | 69.7 |

3) Result of PGE2 Determination

To examine the COX-2 activity by the extracts of *Chrysanthemi Indici. Flos*, intracellular PGE2 level was determined.

The PGE2 production was 3250.3±22.8 pg/ml in the methanol extract at the sample concentration of 25 μg/ml, showing the reduction ratio of 5.1%, as compared to 3425.1±239.6 pg/ml of the control group. The PGE2 production was 3439.5±159.3 pg/ml in the water fraction, but 612.0±85.4 pg/ml in the chloroform fraction, showing the reduction ratio of 82.1% (FIG. 25). Table 16 shows the effects of the extracts and fractions of *Chrysanthemi Indici Flos* on LPS-induced PGE2 expression in RAW 264.7 cells.

TABLE 16

| sample | concentration (μg/ml) | PGE2 expression level (pg/ml) | production ratio (%) |
|---|---|---|---|
| normal group | | 0.0 | 0.0 |
| control group | | 3425.1 ± 239.6 | 100.0 |
| MeOH extract | 25 | 3250.3 ± 22.8 | 94.9 |
| CHCl3 fraction | 25 | 612.0 ± 85.4 | 17.9 |
| Water fraction | 25 | 3439.5 ± 159.3 | 100.4 |

4) Result of COX-2 Determination

The effects of *Chrysanthemi Indici Flos* on COX-2 expression in RAW 264.7 cells were confirmed by Western blot analysis. The experiment was performed at 25 μg/ml of the extract of *Chrysanthemi Indici Flos*. As compared to the control group, each COX-2 expression was 127.0% in the methanol extract, showing the increase ratio of 27.0%, 94.7% in the chloroform fraction, showing the reduction ratio of 5.3%, and 136.3% in the water fraction, showing the increase ratio of 36.3% (FIG. 26). Table 17 shows the effects of the extracts and fractions of *Chrysanthemi Indici Flos* on LPS-induced COX-2 expression in RAW 264.7 cells.

TABLE 17

| sample | concentration (μg/ml) | COX-2 expression level (%/Con) |
|---|---|---|
| normal group | | 23.2 |
| control group | | 100.0 |
| MeOH extract | 25 | 127.0 |
| CHCl3 fraction | 25 | 94.7 |
| Water fraction | 25 | 136.3 |

5) Result of IκB Phosphorylation and Degradation

The inhibitory effect of the extracts of *Chrysanthemi Indici Flos* on LPS-induced IκB phosphorylation and degradation in RAW 264.7 macrophage cell line was confirmed. The experiment was performed at 25 fig/mg of the extract of *Chrysanthemi Indici Flos*. Each IκB expression was 12.6% and 49.6% in the methanol extract and chloroform fraction, showing each reduction ratio of 87.4% and 50.4%, and 28.9% in the water fraction, showing the reduction ratio of 71.1%, indicating the inhibitory effect of the extracts of *Chrysanthemi Indici Flos* on LPS-induced IκB phosphorylation and degradation (FIG. 27). Table 18 shows the effects of the extracts and fractions of *Chrysanthemi Indici Flos* on LPS-induced IκB phosphorylation and degradation in RAW 264.7 cells.

TABLE 18

| sample | concentration (μg/ml) | IκB expression (%) |
|---|---|---|
| normal group | | 100.0 |
| control group | | 0.0 |
| MeOH extract | 25 | 12.6 |
| CHCl3 fraction | 25 | 49.6 |
| Water fraction | 25 | 28.9 |

6) Cytoplasmic and Nuclear NF-κB Expression

The inhibitory effect of the extracts of *Chrysanthemi Indici Flos* on LPS-induced NF-κB nuclear translocation after release from IκB in RAW 264.7 macrophage cell line was confirmed.

At 25 µg/ml of *Chrysanthemi Indici Flos* extract, each p65 expression level was 71.6% and 87.9% in the methanol extract and chloroform fraction, showing each reduction ratio of 28.4% and 12.1%, and 86.1% in water fraction, showing each reduction ratio of 13.9%, as compared to the control group. As such, the extract of *Chrysanthemi Indici Flos* showed inhibitory effect on NF-κB nuclear translocation, namely, a prominent reduction in NF-κB nuclear translocation (FIG. 28). Table 19 shows the effects of the extracts and fractions of *Chrysanthemi Indici Flos* on LPS-induced cytoplasmic and nuclear NF-κB expression in RAW 264.7 cells.

TABLE 19

| sample | concentration (µg/ml) | p65 expression (%) |
| --- | --- | --- |
| normal group | | 58.5 |
| control group | | 100.0 |
| MeOH extract | 25 | 71.6 |
| CHCl$_3$ fraction | 25 | 87.9 |
| Water fraction | 25 | 86.1 |

Example 4

Result of MTS Assay

To confirm the cytotoxicity of the extracts and fractions of *Chrysanthemum boreale* Makino, MTS assay was performed in RAW 264.7 cell using MTS/PMS (Cell Titer 96™ Aqueous Non-Radioactive Cell Proliferation Assay, Cat. G5421-Promega). RAW 264.7 cell was inoculated into 96-well plate at a density of 5×104 cells/mL, and incubated for 24 hrs. The cells were cultured for 24 hrs in DMEM media without serum, containing the extracts of *Chrysanthemum boreale* Makino at the concentrations of 1.25 µg/mL, 2.50 µg/mL, and 5.00 µg/mL. After 24 hrs, the cells were treated with MTS and PMS in a mixing ratio of 20:1, and cultured for 3 hrs. Then, ELISA Reader (Versamax, Molecular Devices Co., U.S.A.) was used to measure absorbance at 490 nm.

Figure 29:
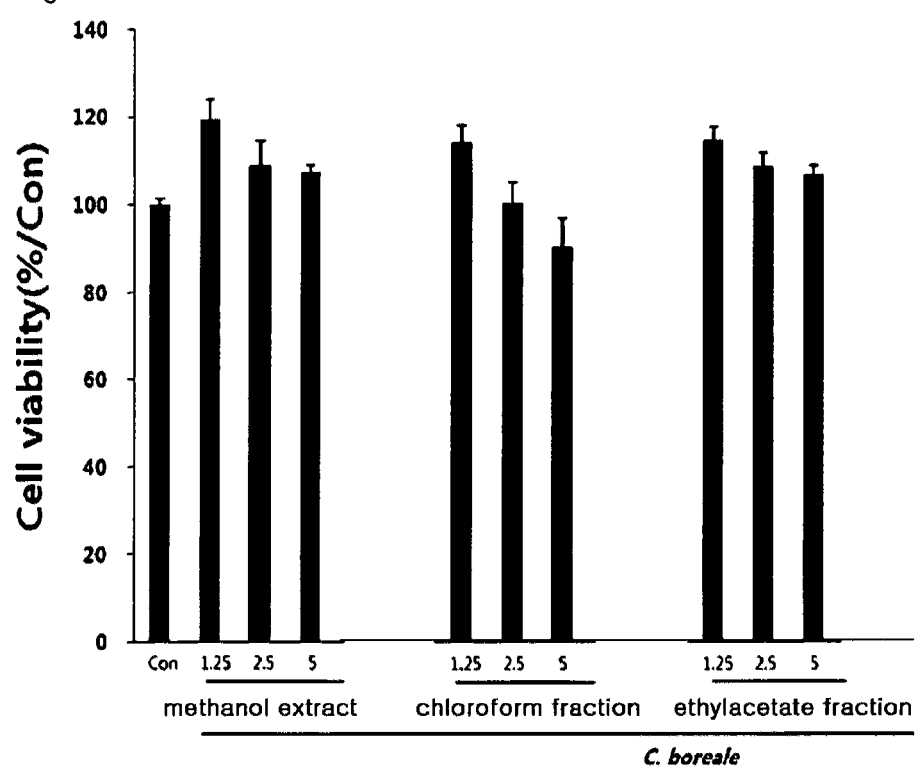
* and FIG. 29 shows the results of MTS assay for cytotoxicity of extracts and fractions of *Chrysanthemum boreale* Makino.

As shown in FIG. 29, it was found that the methanol extract, ethyl acetate fraction, and chloroform fraction hardly affected cell viability of RAW 264.7 at any concentration, indicating no cytotoxicity of the extracts and fractions of *Chrysanthemum boreale* Makino (FIG. 29).

INDUSTRIAL APPLICABILITY

Since the composition according to the present invention has an anti-inflammatory activity, it can be used for the prevention or treatment of inflammatory diseases such as atopic dermatitis, and can also be applied to various fields, including quasi-drugs, cosmetics, foods, and water softeners.

The invention claimed is:

1. A method for treating atopic dermatitis, comprising administering a therapeutically effective amount of extracts of *Chrysanthemum boreale* Makino or fractions thereof to a mammal having atopic dermatitis.

2. The method according to claim 1, wherein the extracts of *Chrysanthemum boreale* Makino or fractions thereof are orally or topically administered.

3. The method according to claim 1, wherein the extracts of *Chrysanthemum boreale* Makino or fractions thereof are formulated in any one formulation selected from the group consisting of tablet, pill, powder, granule, capsule, suspension, liquid for internal use, emulsion, syrup, sterilized aqueous solution, non-aqueous solution, lyophilized formulation, and suppository.

4. The method according to claim 1, wherein the fraction is fractionated by using any solvent selected from the group consisting of chloroform, ethanol, and ethyl acetate, and mixtures thereof.

5. The method according to claim 1, wherein the mammal is a human.

* * * * *